(12) United States Patent
Marino

(10) Patent No.: US 7,963,970 B2
(45) Date of Patent: Jun. 21, 2011

(54) PERCUTANEOUS TRANSPEDICULAR ACCESS, FUSION, DISCECTOMY, AND STABILIZATION SYSTEM AND METHOD

(75) Inventor: James F. Marino, La Jolla, CA (US)

(73) Assignee: Trinity Orthopedics, San Diego, CA (US)

( * ) Notice: Subject to any disclaimer, the term of this patent is extended or adjusted under 35 U.S.C. 154(b) by 498 days.

(21) Appl. No.: 11/562,939

(22) Filed: Nov. 22, 2006

(65) Prior Publication Data
US 2007/0162044 A1    Jul. 12, 2007

(51) Int. Cl.
*A61B 17/58* (2006.01)
*A61B 17/60* (2006.01)
*A61F 2/00* (2006.01)

(52) U.S. Cl. ............... 606/96; 606/98; 606/99; 606/86 A

(58) Field of Classification Search .... 623/17.11–17.16; 606/80, 87, 96–99, 279, 86, 79, 104, 108, 606/86 A, 86 R, 90
See application file for complete search history.

(56) References Cited

U.S. PATENT DOCUMENTS

| | | | |
|---|---|---|---|
| 5,242,444 A * | 9/1993 | MacMillan | 606/86 R |
| 5,423,826 A | 6/1995 | Coates et al. | |
| 5,569,248 A | 10/1996 | Mathews | |
| 6,080,157 A | 6/2000 | Cathro et al. | |
| 6,224,603 B1 | 5/2001 | Marino | |
| 6,358,254 B1 | 3/2002 | Anderson | |
| 6,485,518 B1 | 11/2002 | Cornwall et al. | |
| 6,520,967 B1 | 2/2003 | Cauthen | |
| 6,575,899 B1 | 6/2003 | Foley et al. | |
| 6,814,737 B2 | 11/2004 | Cauthen | |
| 2003/0004517 A1 | 1/2003 | Anderson | |
| 2003/0191474 A1 | 10/2003 | Cragg et al. | |
| 2003/0199871 A1 | 10/2003 | Foley et al. | |
| 2003/0212400 A1 | 11/2003 | Bloemer et al. | |
| 2004/0092933 A1 * | 5/2004 | Shaolian et al. | 606/61 |
| 2005/0125066 A1 | 6/2005 | McAfee | |
| 2005/0187556 A1 | 8/2005 | Stack et al. | |
| 2005/0283246 A1 * | 12/2005 | Cauthen et al. | 623/17.16 |
| 2006/0115055 A1 | 6/2006 | Marino | |
| 2007/0127626 A1 | 6/2007 | Marino | |

FOREIGN PATENT DOCUMENTS

| | | |
|---|---|---|
| WO | WO 00/48521 | 8/2000 |
| WO | WO 00/62684 | 10/2000 |
| WO | WO 01/41681 | 6/2001 |
| WO | WO 2006/116606 | 11/2006 |
| WO | WO 2007/062132 | 5/2007 |
| WO | WO 2007/062133 | 5/2007 |

* cited by examiner

*Primary Examiner* — Eduardo C Robert
*Assistant Examiner* — Christina Negrelli
(74) *Attorney, Agent, or Firm* — Fred C. Hernandez; Mintz, Levin, Cohn, Ferris, Glovsky and Popeo P.C.

(57) ABSTRACT

Apparatus and methods for accessing an inferior vertebra, a superior vertebra, and a disc space therebetween via a transpedicular approach in the inferior vertebra that may include creating a channel normal to the pedicle and using an offset guide to create a second transpedicular channel at an angle to the first, normal pedicle channel where the second transpedicular channel passes into the inferior vertebra, superior vertebra, or the disc space therebetween.

37 Claims, 33 Drawing Sheets

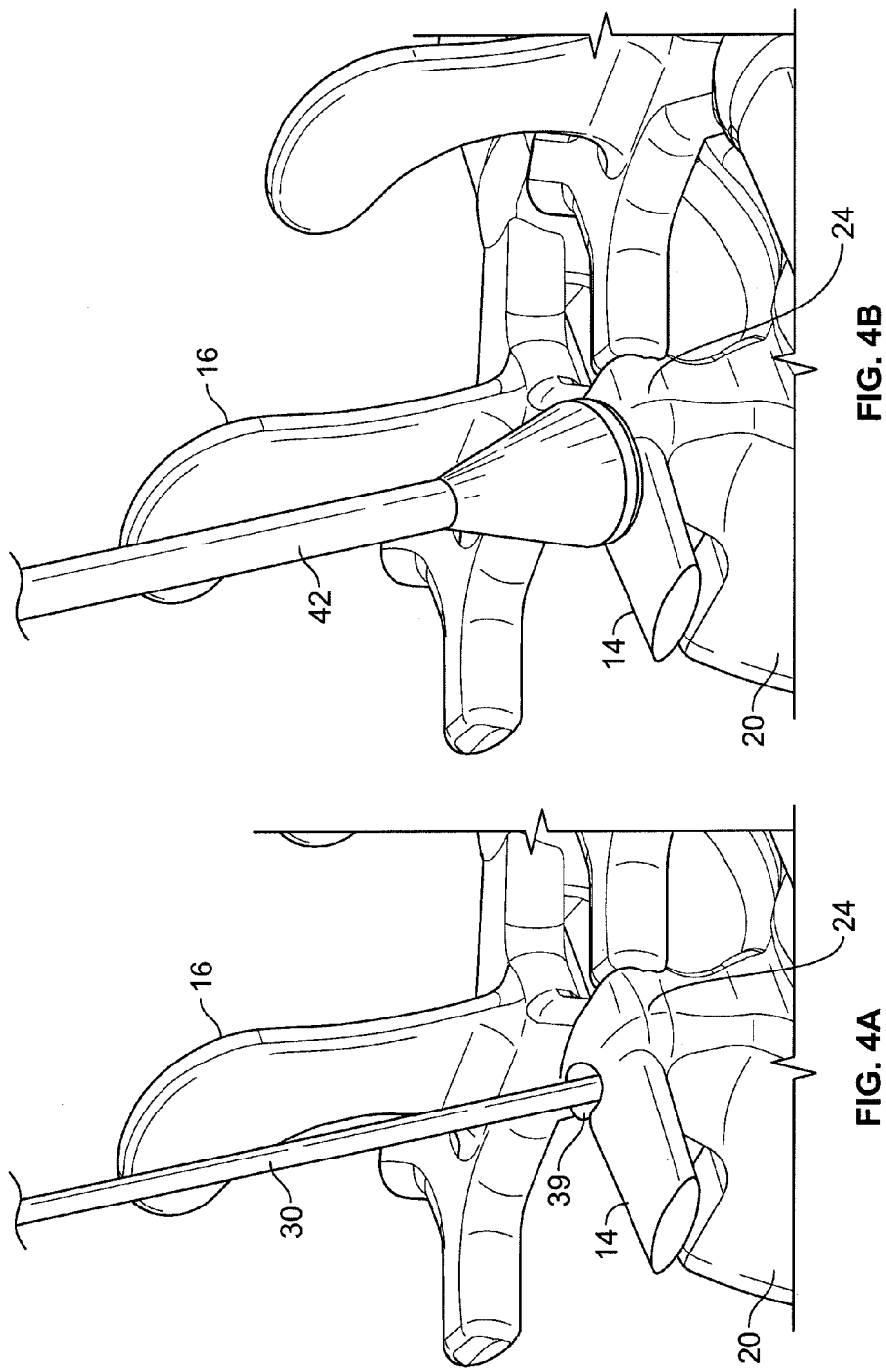

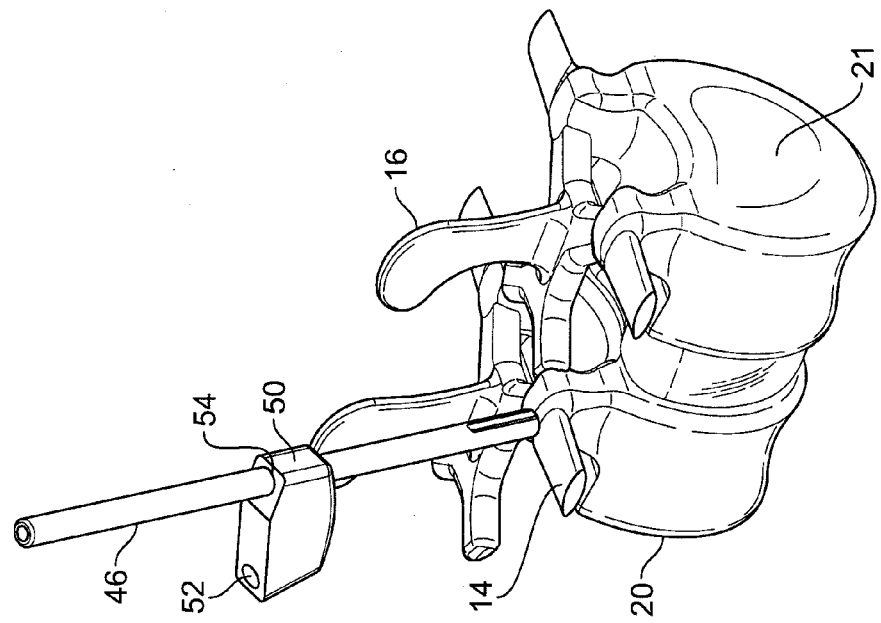
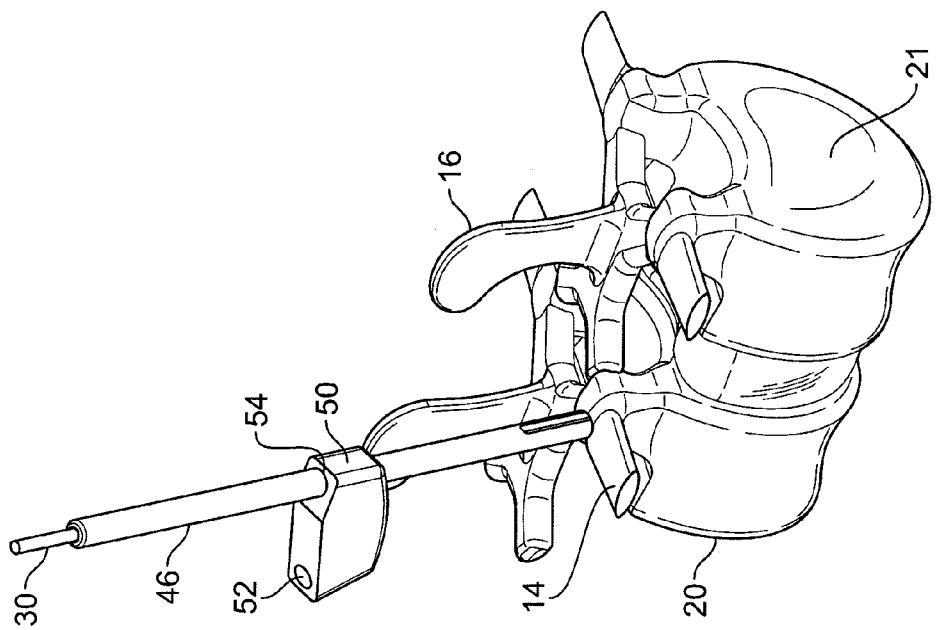

PERCUTANEOUS TRANSPEDICULAR ACCESS, FUSION, DISCECTOMY, AND STABILIZATION SYSTEM AND METHOD

BACKGROUND

1. Field of the Invention

The invention relates generally to orthopedic boney fusion, discectomy, and stabilization systems and methods, and more particularly, to percutaneous fusion, discectomy, and stabilization systems and methods.

2. Description of Related Art

It is desirable to provide a percutaneous fusion, discectomy, and stabilization system and method that limits or prevents the risks of nerve injury or epineural fibrosis. The present invention provides such a system and method.

SUMMARY OF THE INVENTION

The present invention includes apparatus and methods for accessing the disc space between an inferior and superior vertebra via a transpedicular approach in the inferior vertebra including creating a channel normal to the pedicle and using an offset guide to create a second transpedicular channel at an angle to the first, normal pedicle channel where the second transpedicular channel passes into the disc space.

BRIEF DESCRIPTION OF THE DRAWINGS

The features, objects, and advantages of the present invention will become more apparent from the detailed description set forth below when taken in conjunction with the drawings in which like reference characters identify correspondingly throughout and wherein:

FIG. 4A is a simplified isometric view of the vertebrae pair where the cannulated reamer and the cannula have been removed leaving the guide pin inserted in the bored pedicle according to various embodiments;

FIG. 4B is a simplified isometric view of the vertebrae pair shown in FIG. 4A further including a cannulated spot facer inserted over the guide pin, the spot facer being operatively advanced into the pedicle to enlarge the bore formed in the pedicle according to various embodiments;

FIG. 5A is a simplified sagittal view of the vertebrae pair shown in FIG. 4D further including a transpedicular channel alignment tool inserted over the cannula according to various embodiments;

FIG. 5B is a simplified sagittal view of the vertebrae pair where the guide pin has been removed leaving the cannula inserted in pedicle bore and transpedicular channel alignment tool inserted over the cannula according to various embodiments;

DETAILED DESCRIPTION

Throughout this description, embodiments and variations are described for the purpose of illustrating uses and implementations of the invention. The illustrative description should be understood as presenting examples of the invention, rather than as limiting the scope of the invention.

Figure 1B:
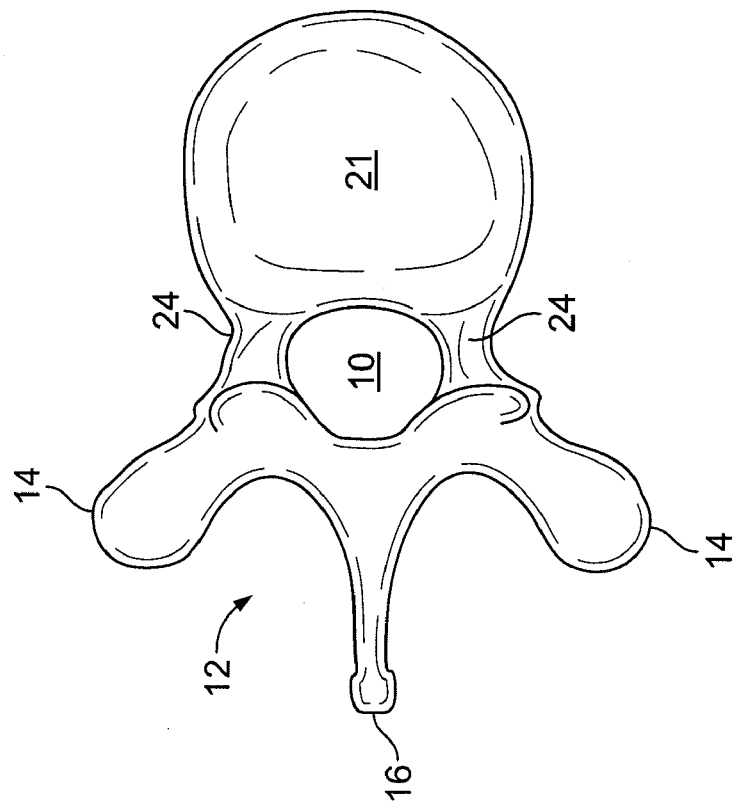
FIG. 1B is a simplified, sectional coronal view a vertebrae.
Figure 1A:
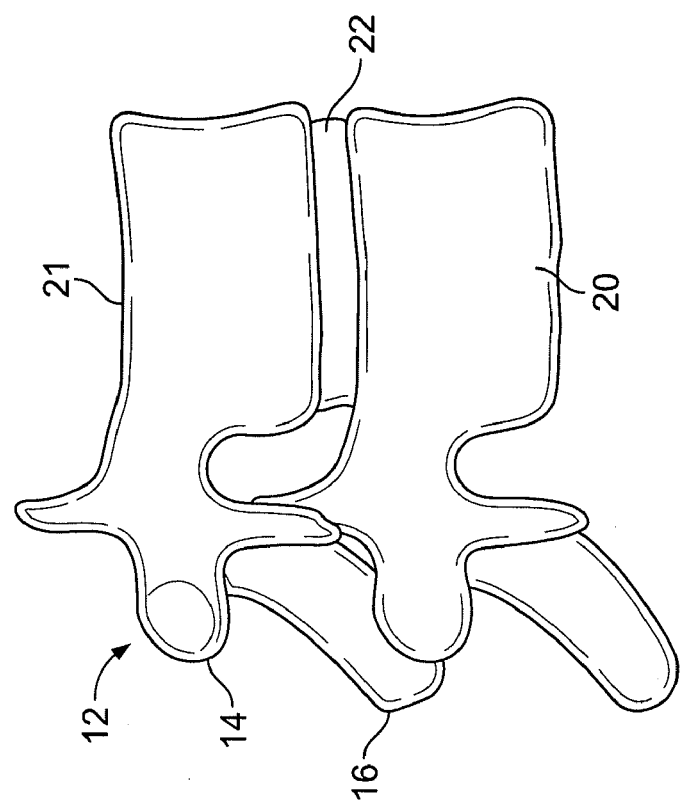
FIG. 1A is a simplified sagittal view of a vertebrae pair.

FIG. 1A is a simplified sagittal view of a vertebrae pair 20, 21. FIG. 1B is a simplified, sectional coronal view of the vertebrae 21 of the vertebrae pair shown in FIG. 1A. Each vertebra 20, 21 includes lamina 12, transverse processes 14, a spinous process 16, central 10, and pedicles 24. A disc 22 comprised of an annulus and disc nucleus (not shown) is located between the vertebrae pair 20, 21. Due to disc degeneration, expulsion, annulus tears, or other conditions, the spinal cord that passes through the central canal 10 may become compressed causing patient discomfort. It may be desirable to modify or fix the spatial relationship between the vertebrae pair 20, 21. FIGS. 2A to 8F present various apparatus and methods for accessing the vertebrae pair 20, 21 to perform a surgical procedure.

In an embodiment, access to the disc space 22 or superior vertebra 21 is achieved via a channel formed in inferior vertebra's 20 pedicle 24. FIGS. 2A to 7D present methods and apparatus for forming such a channel according to various embodiments. In this embodiment a normal channel is first formed in the inferior vertebrae 20's pedicle. Then a second, offset channel is formed in the inferior vertebrae 20 based on the formed normal channel. The second, offset channel may enable access the disc space 22 or superior vertebrae 21.

Figure 2A:
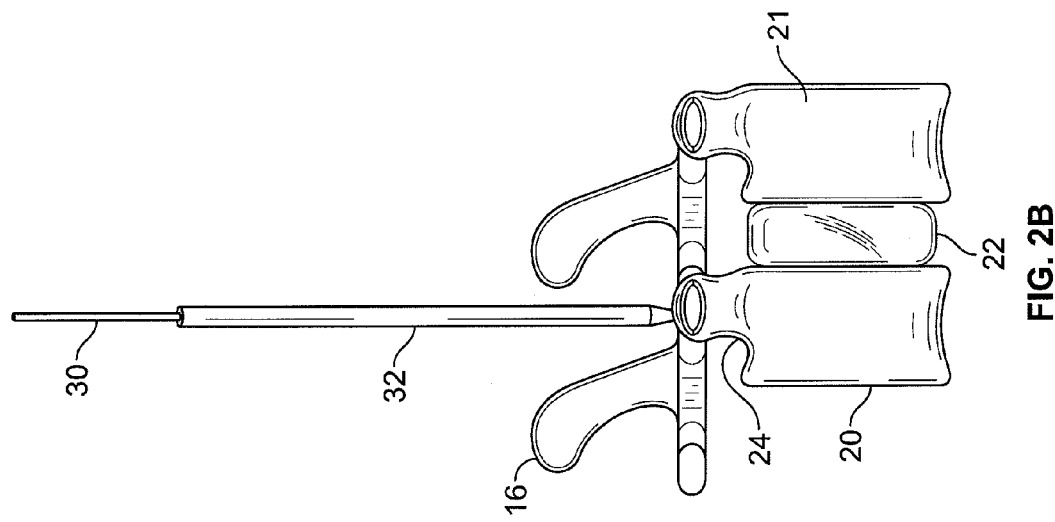
FIG. 2A is a simplified coronal view of the vertebrae pair including a guide pin and support sleeve, the guide pin being inserted into a pedicle according to various embodiments.
Figure 2B:
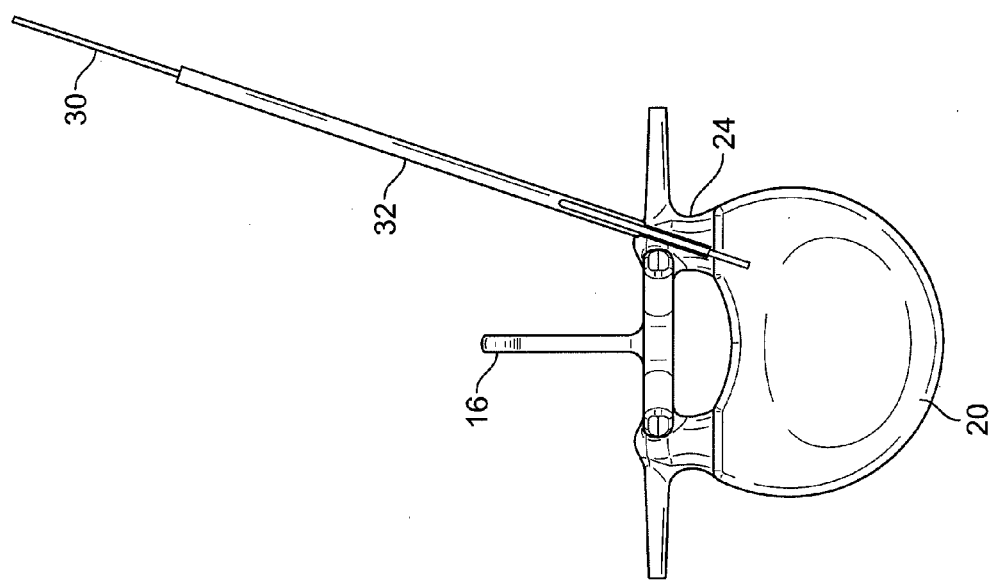
FIG. 2B is a simplified sagittal view of the vertebrae pair including a guide pin and support sleeve, the guide pin being inserted into a pedicle as shown in FIG. 2A.
Figure 2D:
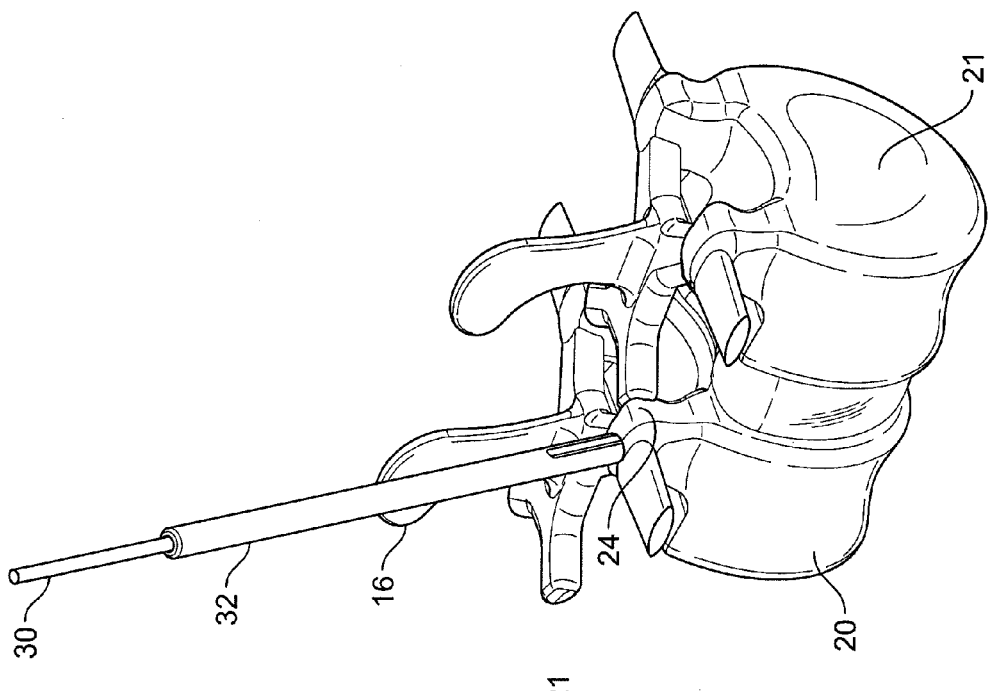
FIG. 2D is a simplified isometric view of the vertebrae pair including a guide pin and support sleeve, the guide pin being inserted into a pedicle as shown in FIG. 2A.
Figure 2C:
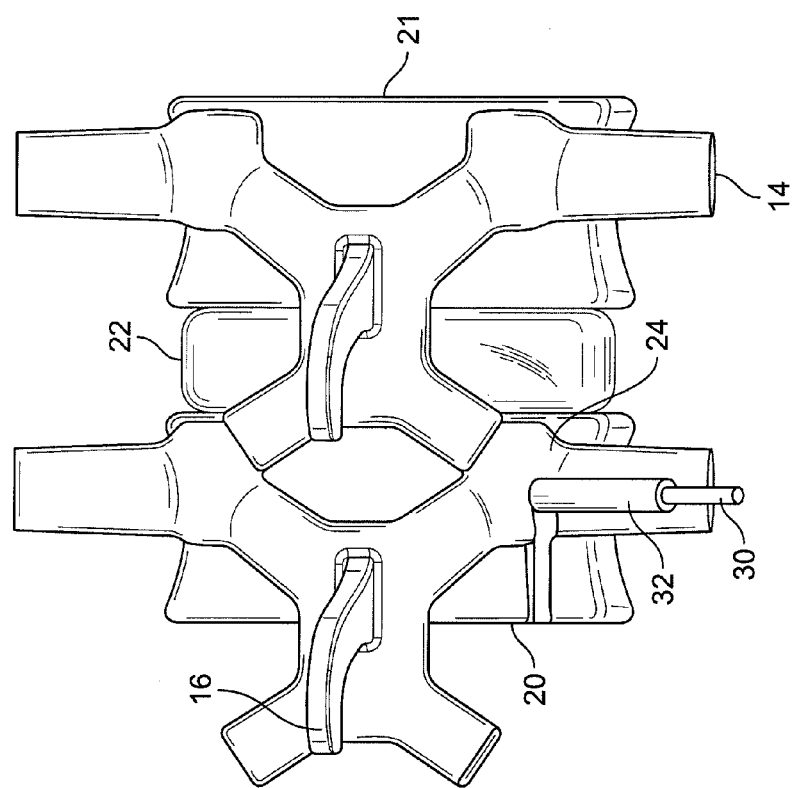
FIG. 2C is a simplified posterior view of the vertebrae pair including a guide pin and support sleeve, the guide pin being inserted into a pedicle as shown in FIG. 2A.

FIG. 2A is a simplified coronal view, FIG. 2B is a simplified sagittal view, FIG. 2C is a simplified posterior view, and FIG. 2D is an isometric view of the vertebrae pair 20, 21 including a guide pin or wire 30 and support sleeve 32 according to various embodiments. In this embodiment, the guide pin 30 is inserted at a posterior, lateral angle from the coronal view and normal to the vertebrae 20 from the sagittal view. The guide pin extends into the vertebrae 20 pedicle 24 while not violating the pedicle wall. In addition in an embodiment a support sleeve 32 may be inserted over the guide pin 30. The support sleeve 32 may be a thin walled cannula in an embodiment of the present invention.

Figure 3A:
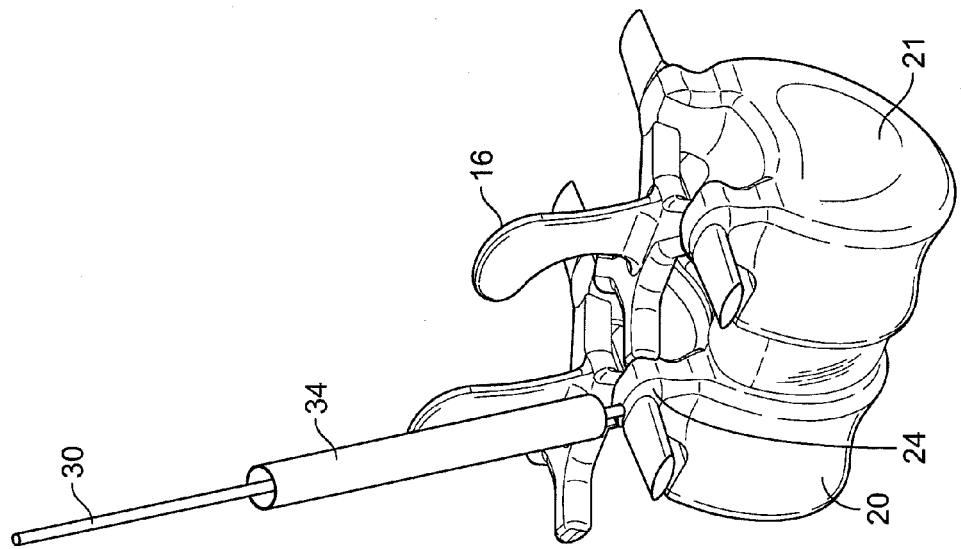
FIG. 3A is a simplified isometric view of the vertebrae pair shown in FIG. 2D further including an obturator and cannula inserted over the guide pin and support sleeve, the obturator being advanced toward a pedicle to create a tissue pathway to the pedicle according to various embodiments.
Figure 3B:
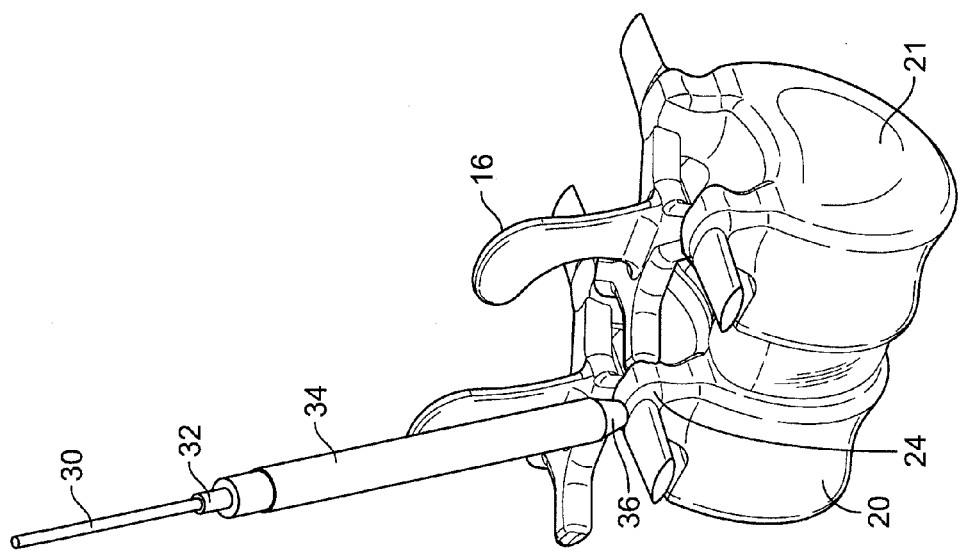
FIG. 3B is a simplified isometric view of the vertebrae pair where the obturator and guide sleeve have been removed leaving the guide pin inserted into the pedicle with the cannula over the guide pin according to various embodiments.
Figure 3C:
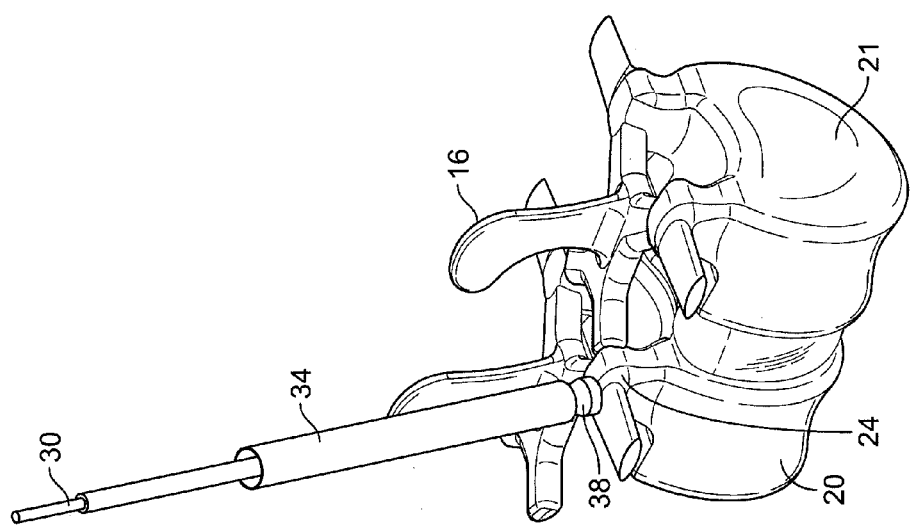
FIG. 3C is a simplified isometric view of the vertebrae pair shown in FIG. 3B further including a cannulated reamer inserted over the guide pin and within the cannula, the reamer being operatively advanced into the pedicle to form a bore in the pedicle according to various embodiments.

FIG. 3A is a simplified isometric view of the vertebrae pair 20, 21 shown in FIG. 2D further including an obturator 36 and cannula 34 inserted over the guide pin 30 and support sleeve 32. In an embodiment the obturator 36 may be advanced toward a pedicle 24 to create a tissue pathway to the pedicle 24. FIG. 3B is a simplified isometric view of the vertebrae pair 20, 21 where the obturator 36 and guide sleeve 32 have been removed leaving the guide pin 30 inserted into the pedicle with the cannula 34 over the guide pin 30. FIG. 3C is a simplified isometric view of the vertebrae pair 20, 21 shown in FIG. 3B further including a cannulated reamer 38 inserted over the guide pin 30 and within the cannula 34. In an embodiment, the reamer 38 may be operatively advanced into the pedicle 24 to form a bore in the pedicle 24. In an embodiment the reamer 38 may have about a 5 mm diameter and about an 8 mm depth stop. In this embodiment, the reamer 38 may be used to form an approximately 10 mm deep, 5 mm in diameter bore (39 shown in FIG. 4A) in the pedicle 24, the bore 39 axis being approximately normal to the coronal plane of vertebrae 20. In this embodiment the cannula 34 may have a diameter of about 8.5 mm.

FIG. 4A is a simplified isometric view of the vertebrae pair 20, 21 where the cannulated reamer 38 and the cannula 34 have been removed leaving the guide pin 30 inserted in the bored pedicle according to various embodiments. FIG. 4B is a simplified isometric view of the vertebrae pair 20, 21 shown in FIG. 4A further including a cannulated spot facer 42 inserted over the guide pin 30. In an embodiment, the spot facer 42 may be operatively advanced into the pedicle 24 to enlarge an upper section of the bore 39 formed in the pedicle 24. In an embodiment the spot facer 42 has about a 12 mm diameter with a projected wall. In an embodiment the spot facer 42 forms a larger upper bore section to be occupied by a polyaxial or monoaxial pedicle receiving section, the section moveably coupled or couplable to a pedicle screw head.

Figure 4D:
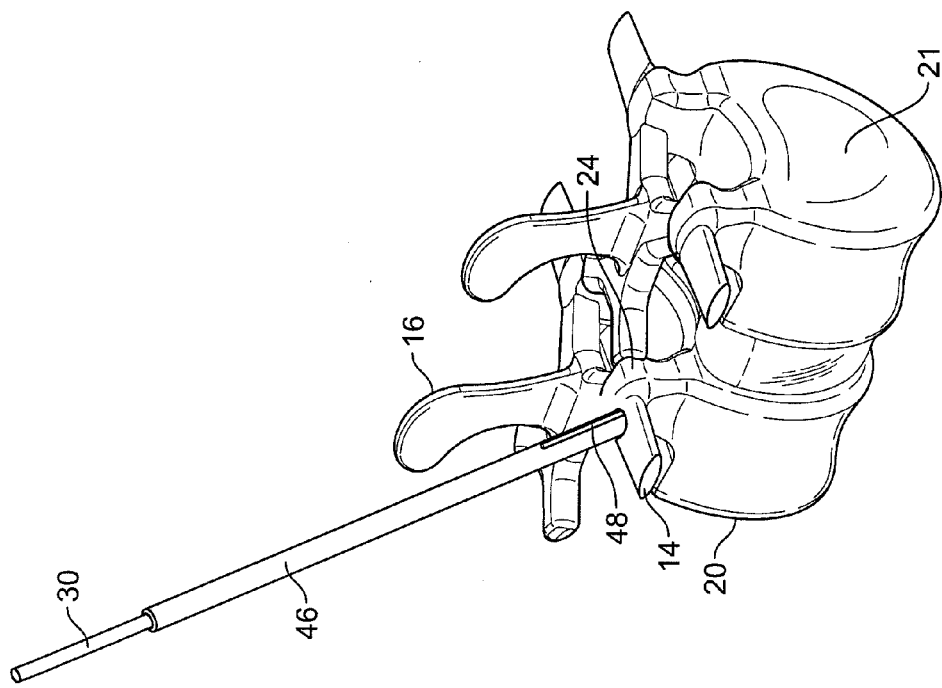
FIG. 4D is a simplified isometric view of the vertebrae pair shown in FIG. 4C further including a slotted cannula inserted over the guide pin, the cannula being advanced into the pedicle bore in the pedicle according to various embodiments.
Figure 4C:
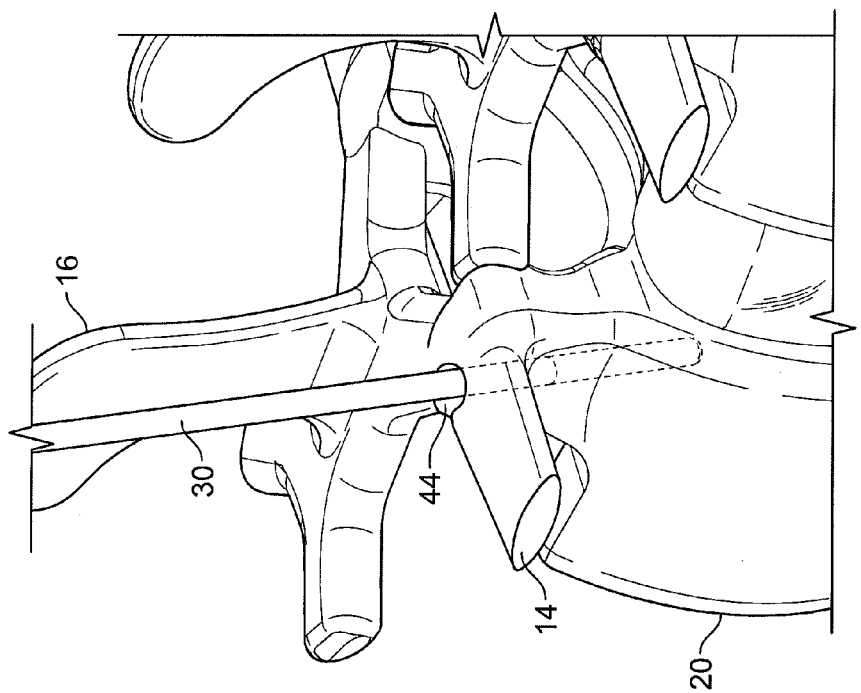
FIG. 4C is a simplified isometric view of the vertebrae pair where the cannulated spot facer has been removed leaving the guide pin inserted in the enlarged, bored pedicle according to various embodiments.

FIG. 4C is a simplified isometric view of the vertebrae pair 20, 21 where the cannulated spot facer 42 has been removed leaving the guide pin 30 inserted in the enlarged, bored pedicle according to various embodiments. FIG. 4D is a simplified isometric view of the vertebrae pair 20, 21 shown in FIG. 4C further including a slotted cannula 46 inserted over the guide pin 30, the cannula 46 being advanced into the pedicle bore 44 in the pedicle 24 according to various embodiments. FIG. 5A is a simplified sagittal view of the vertebrae pair 20, 21 shown in FIG. 4D further including a transpedicular channel alignment tool 50 inserted over the cannula according to various embodiments. In an embodiment the alignment tool 50 is aligned along the caudal-cephalad (sagittal plane). The tool 50 includes a normal port 54 and an offset port 52. The normal port is sized to receive the guide pin 30 or slotted cannula 46.

Figures 5C, 5D:
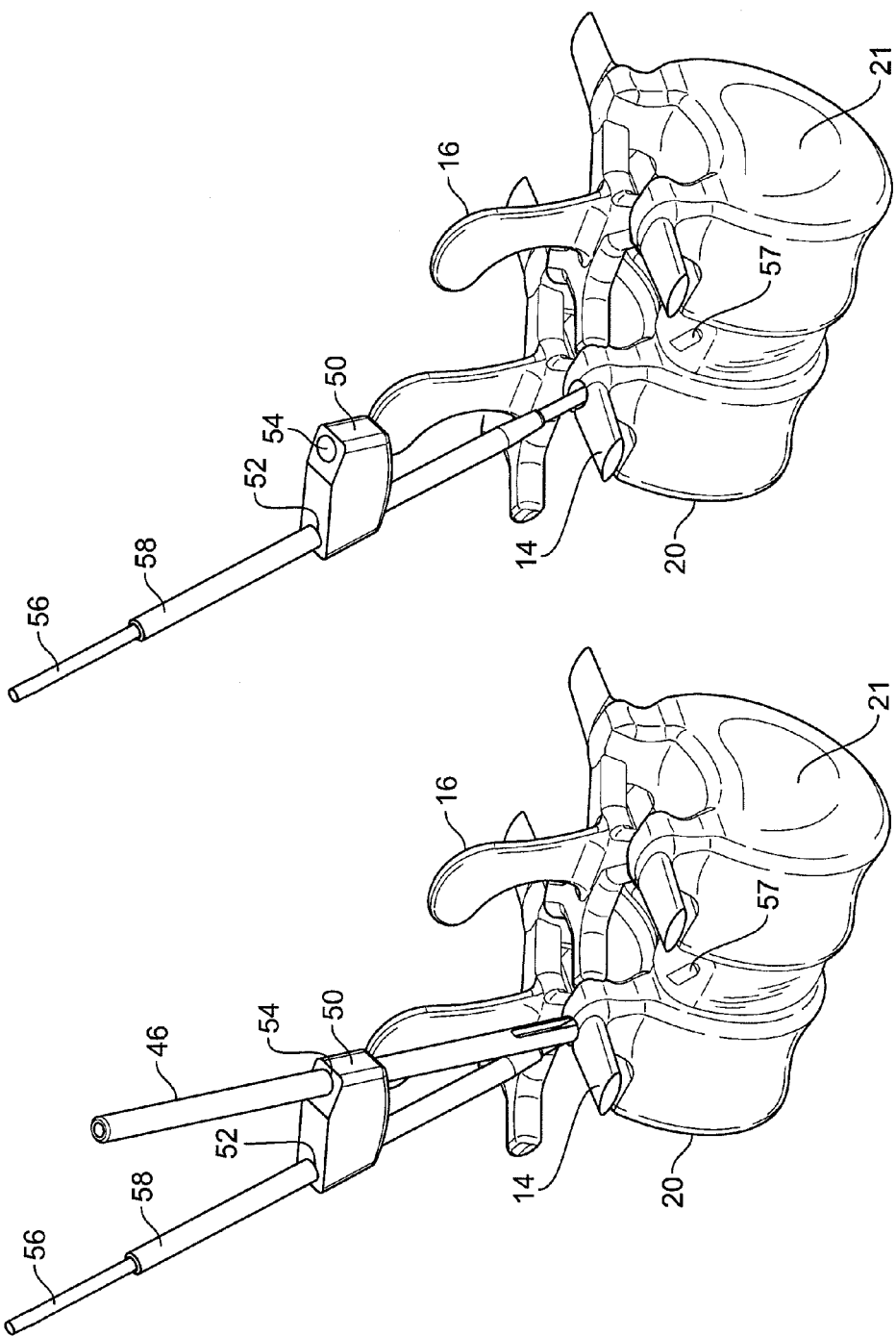
FIG. 5C is a simplified sagittal view of the vertebrae pair shown in FIG. 5B further including a guide pin with support sleeve, the guide pin and support sleeve being inserted through the transpedicular channel alignment tool's offset guide port and the guide pin advanced at an angle offset from normal to the vertebrae pair into disc space according to various embodiments.
FIG. 5D is a simplified sagittal view of the vertebrae pair shown in FIG. 5C where the cannula in the transpedicular channel alignment tool's normal guide port has been removed leaving the guide pin and support sleeve inserted through the transpedicular channel alignment tool's offset guide port and the guide pin advanced at the offset angle according to various embodiments.

FIG. 5B is a simplified sagittal view of the vertebrae pair 20, 21 where the guide pin 30 has been removed leaving the slotted cannula 46 inserted in pedicle bore 44 and transpedicular channel alignment tool 50 inserted over the cannula 46 according to various embodiments. In this embodiment the alignment tool's 50 normal port 54 is sized to receive the slotted cannula 46. In an embodiment the offset port 52 is oriented an angle to the normal port 54 about 20 degrees. FIG. 5C is a simplified sagittal view of the vertebrae pair 20, 21 shown in FIG. 5B further including an offset guide pin 56 with offset support sleeve 58 inserted through the transpedicular channel alignment tool's 50 offset guide port 52. In an embodiment the offset guide pin 56 is advanced at the offset angle from normal to the vertebrae pair 20, 21 into disc space. In an embodiment one or more X-rays may be taken and reviewed to determine whether the offset guide pin 56 is proceeding along a desired pathway in the pedicle 24 prior to advancement into the disc space 22.

Figures 6A, 6B:
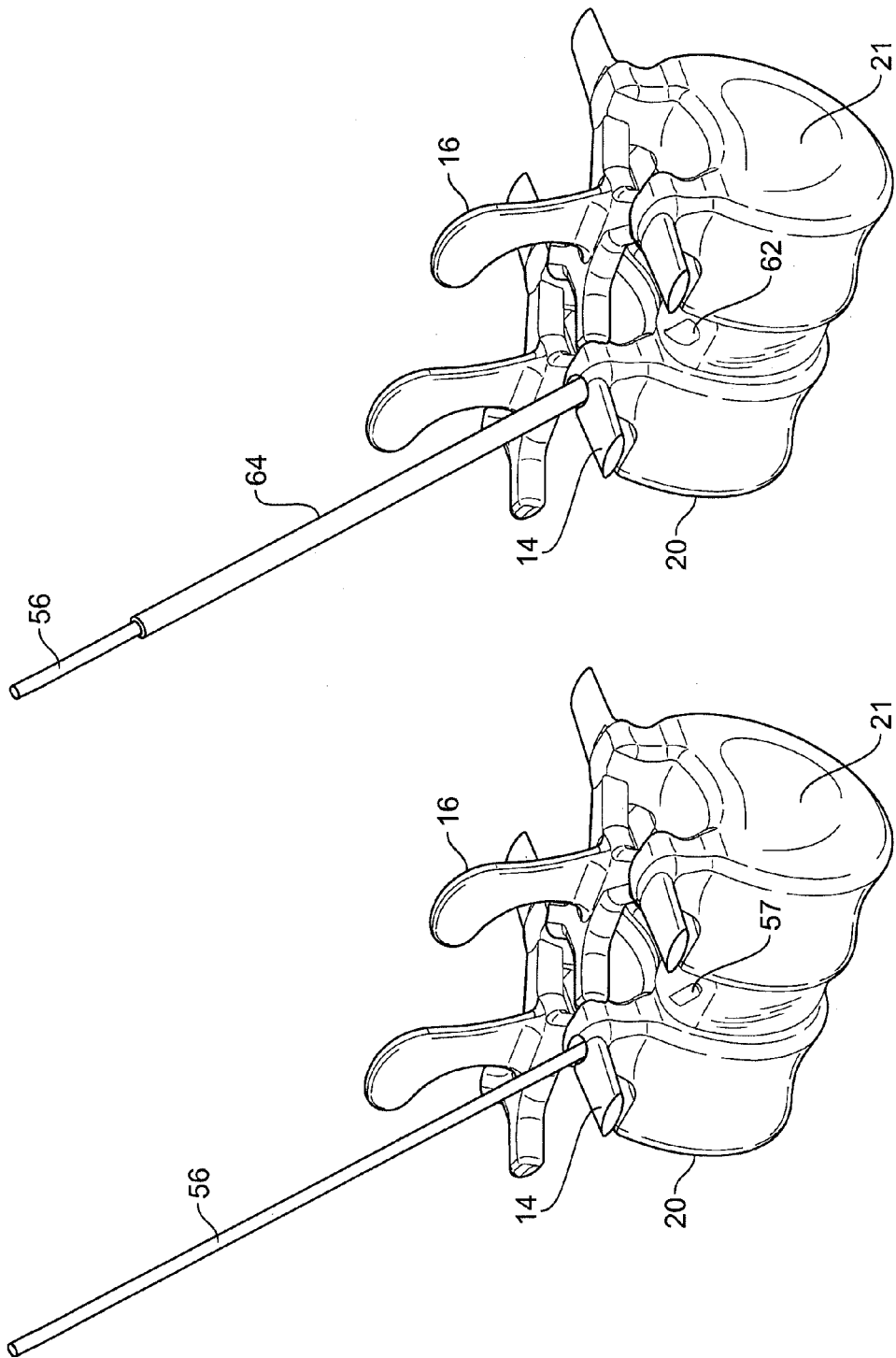
FIG. 6A is a simplified sagittal view of the vertebrae pair shown in FIG. 5D where support sleeve in the transpedicular channel alignment tool's offset guide port and the alignment tool have been removed leaving the guide pin inserted through a transpedicular channel to the disc space according to various embodiments.
FIG. 6B is a simplified sagittal view of the vertebrae pair shown in FIG. 6A further including a cannulated reamer within a cannula inserted over the offset guide pin, the reamer being operatively advanced into disc space via the transpedicular channel to enlarge the channel according to various embodiments.

FIG. 5D is a simplified sagittal view of the vertebrae pair 20, 21 shown in FIG. 5C where the cannula 46 in the transpedicular channel alignment tool's normal guide port 54 has been removed leaving the guide pin and support sleeve inserted through the transpedicular channel alignment tool's 50 offset guide port 52 and the offset guide pin 56 advanced at the offset angle according to various embodiments. FIG. 6A is a simplified sagittal view of the vertebrae pair 20, 21 shown in FIG. 5D where the offset support sleeve 58 in the transpedicular channel alignment tool's 50 offset guide port 52 and the alignment tool 50 have been removed leaving the offset guide pin 56 inserted through a transpedicular channel to the disc space 22 according to various embodiments. As shown, the guide pin 56 tip 57 is projecting into the disc space 22. In an embodiment the transpedicular channel may be enlarged to enable different procedures to be performed in the disc space 22. The transpedicular channel is not adjacent or near any nerve pathways in an embodiment, reducing the risk of nerve related injuries due a procedure being performed in the disc space 22.

Figure 6C:
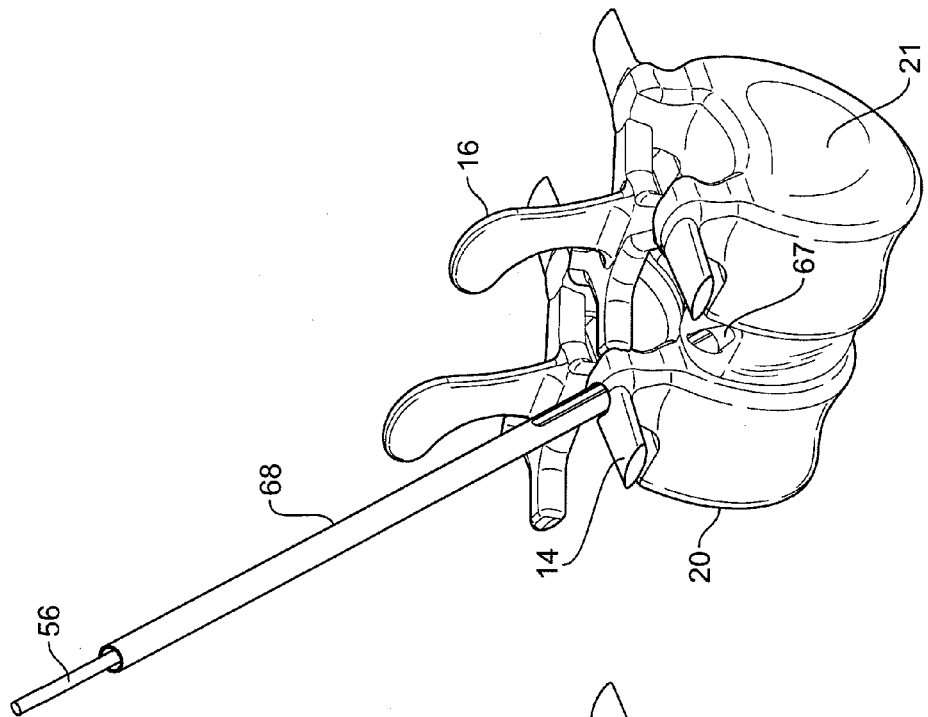
FIG. 6C is a simplified sagittal view of the vertebrae pair shown in FIG. 6B where cannulated reamer and the cannula have been removed leaving the guide pin inserted through the enlarged transpedicular channel to the disc space according to various embodiments.

FIG. 6B is a simplified sagittal view of the vertebrae pair 20, 21 shown in FIG. 6A further including a cannulated reamer 62 within a cannula 64 inserted over the offset guide pin 56. In an embodiment the reamer 62 may be operatively advanced into disc space via the transpedicular channel to enlarge the channel 66. In an embodiment the reamer 62 may be about a 5.5 mm reamer to form a 5.5 mm diameter channel 66 from the pedicle 24 of the inferior vertebra 20 to the disc space 22. FIG. 6C is a simplified sagittal view of the vertebrae pair 20, 21 shown in FIG. 6B where the cannulated reamer 62 and the cannula 64 have been removed leaving the guide pin 56 inserted through the enlarged transpedicular channel 66 to the disc space 22.

Figure 6D:
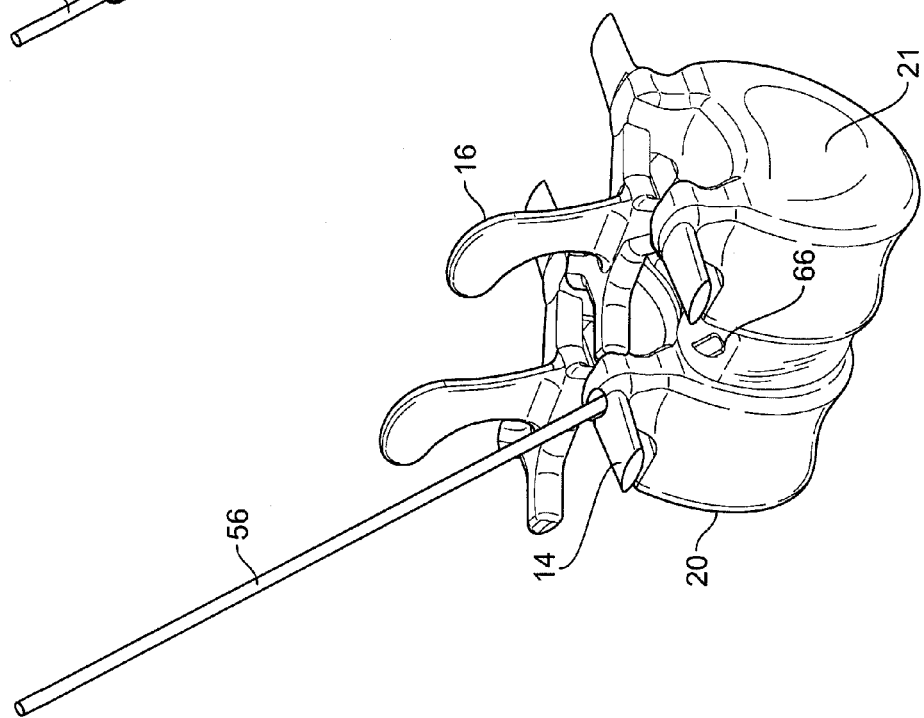
FIG. 6D is a simplified sagittal view of the vertebrae pair shown in FIG. 6C further including a cannula inserted over the offset guide pin, the cannula being advanced into disc space via the transpedicular channel according to various embodiments.
Figure 6E:
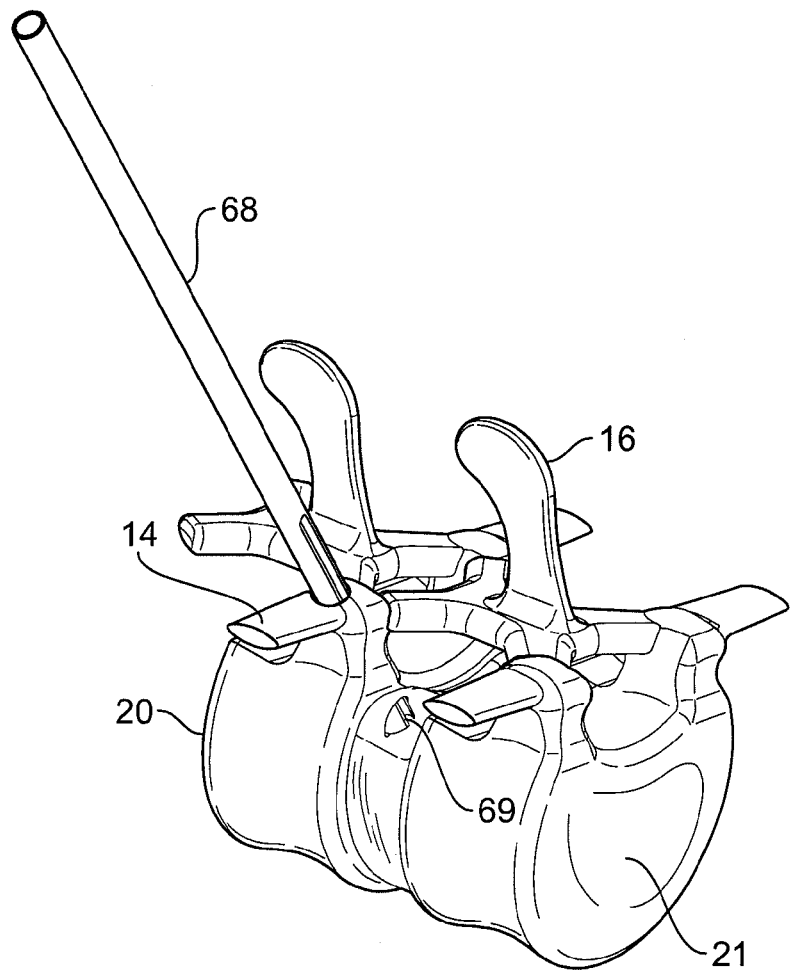
FIG. 6E is a simplified sagittal view of the vertebrae pair shown in FIG. 6B where the guide pin has been removed leaving the offset cannula in enlarged transpedicular channel to the disc space according to various embodiments.
Figure 6F:
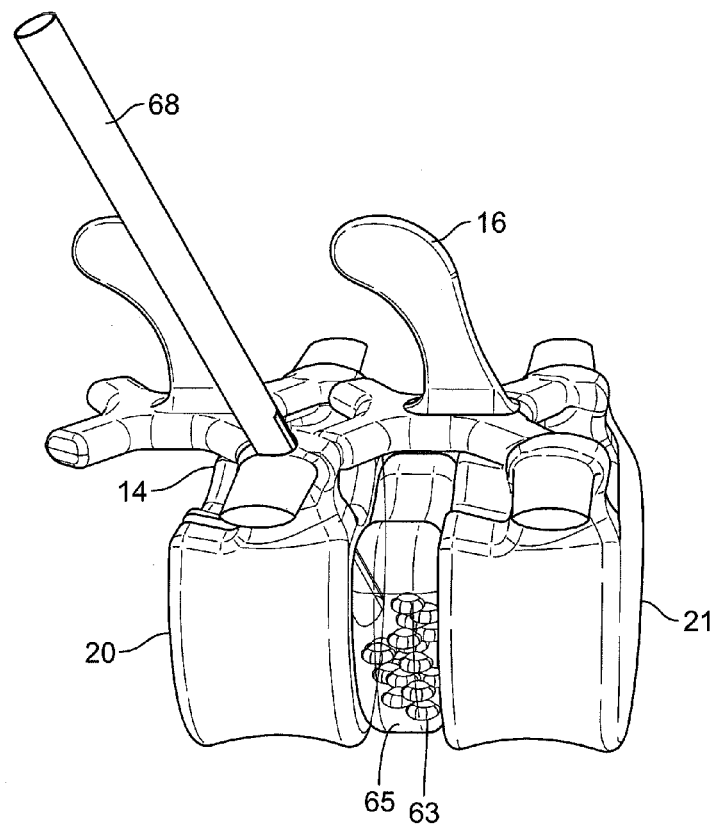
FIG. 6F is a simplified sagittal view of the vertebrae pair shown in FIG. 6B where bone granules have been inserted into the disc space via the cannula according to various embodiments.

FIG. 6D is a simplified sagittal view of the vertebrae pair shown in FIG. 6C further including a slotted cannula 68 and obturator 67 inserted over the offset guide pin 56. In an embodiment a tapered obturator 67 within a slotted, thin walled cannula 68 are inserted over the offset guide pin 56 into the disc space 22 via the transpedicular channel. In an embodiment the slotted cannula 68 has about a 5.5 mm diameter to be accommodated by the channel 66 formed by the reamer 62. FIG. 6E is a simplified sagittal view of the vertebrae pair 20,21 shown in FIG. 6D where the guide pin 56 and obturator 67 have been removed leaving the slotted, offset cannula 68 in the enlarged transpedicular channel 66 to the disc space 22 according to various embodiments. Various tools and instruments may be employed via the cannula 68 to perform procedures within the disc space 22 including discectomy, annulus closure or repair, fusion implantation including implants, bone growth materials, and allograft material. For example, FIG. 6F is a simplified sagittal view of the vertebrae pair shown in FIG. 6B where bone granules 63 (allograft material) packed with a powered material 65 have been inserted into the disc space 22 via the cannula 68 according to various embodiments.

Figure 6G:
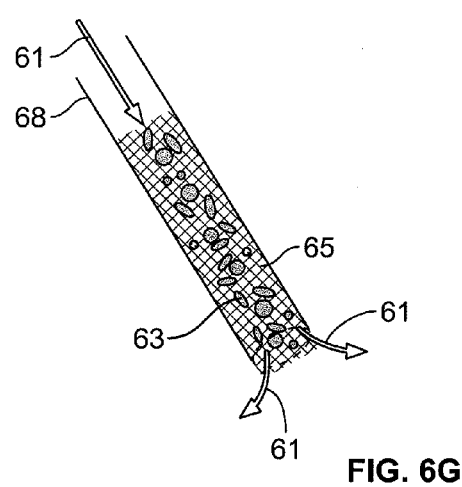
FIGS. 6G and 6I depict the force vectors as applied to a compacted granular-powered material within a cannula and a disc space according to various embodiments.
Figure 6I:
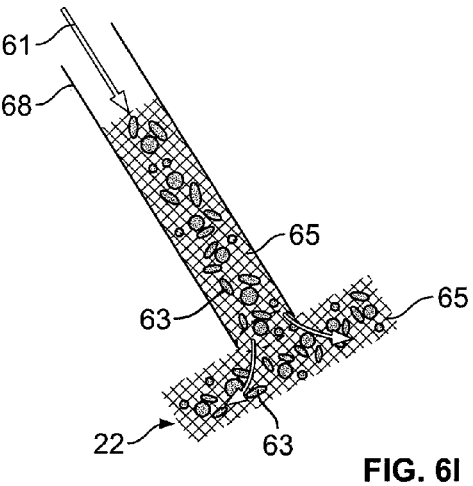

FIGS. 6G and 6I depict the force vectors 61 as applied to the compacted granular-powered material 63,65 within a cannula 68 and disc space 22. The bone granules 63 may be packed with a powered material 65 to facilitate their passage into the disc space 22 via the cannula 68. In particular the powered material 65 helps prevent the larger particles 63 from binding together and becoming wedged within a cannula 68 as passed there-through. As shown in FIG. 6G the force vectors 61 may split at the cannula distal end as the powered material 65 and granules 63 become disassociated as the cannula 68 walls prevent earlier such disassociation.

In an embodiment the powered material may be calcium sulfate, Plaster of Paris (calcium sulfate hemi-hydrate), finely pulverized cortical bone with decalcification, or similar fine material safe for insertion into the disc space 22 and possible absorption. In an embodiment the granules 63 may be a granular cortical or structural allograft material. The granules 63 may have a generally spherical geometry and maximum cross sectional area smaller than the cross section area of a delivery cannula 68. In an embodiment a binding agent may be employed to bind the powered material 65 and granules 65 including evaporated or saturated sugar or starch solution. The granular composite (65 and 63 and binding agent) may be fashioned into cylindrical pellets using a thermal and pressure modulated curing process. The resultant pellets may then be sterilely packaged.

In an embodiment the cylindrical pellets may be packaged within a thin walled polymer material, e.g. "straws". Such packages (pellets with straws) may be inserted into a delivery cannula 68 or alternatively placed in automated delivery devices or systems. Such cylindrical pellets may be driven via linear forces 61 through the length of the cannula 68, without pellet dissociation or granular element binding. As noted once the composite (63, 65) exits the supportive cannula 68 walls additional forces (e.g. impact loading upon vertebra 20, 21 and disc annulus 22 may dissociate the granules 63. Such dissociation may form an expanding sphere of composite material, the sphere capable of effecting bone displacement or fracture site reduction and having load bearing capacity proportional to the material 63 density. The powered material 61-granules 65 composition may be used in cannulated procedures for intervertebral disc arthrodesis, vertebroplasty applications for vertebral compression fractures, periarticular depression fracture reductions and bone grafting, bone cyst therapies, etc.

Figure 7A:
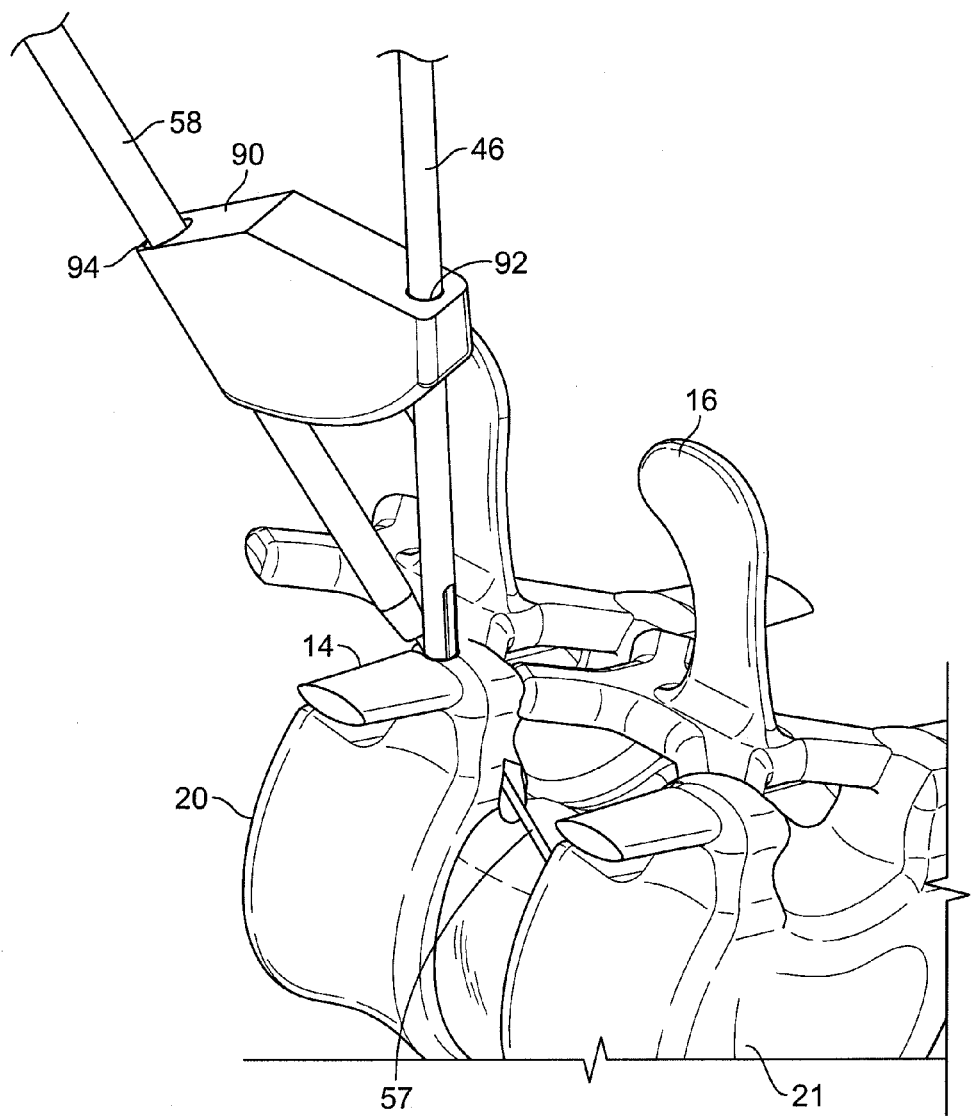
FIG. 7A is a simplified isometric view of the vertebrae pair shown in FIG. 4D further including a guide pin with support sleeve and second transpedicular channel alignment tool, the guide pin and support sleeve being inserted through the second transpedicular channel alignment tool's offset guide port and the guide pin advanced at a second offset angle from normal to the vertebrae pair into disc space according to various embodiments.
Figure 7B:
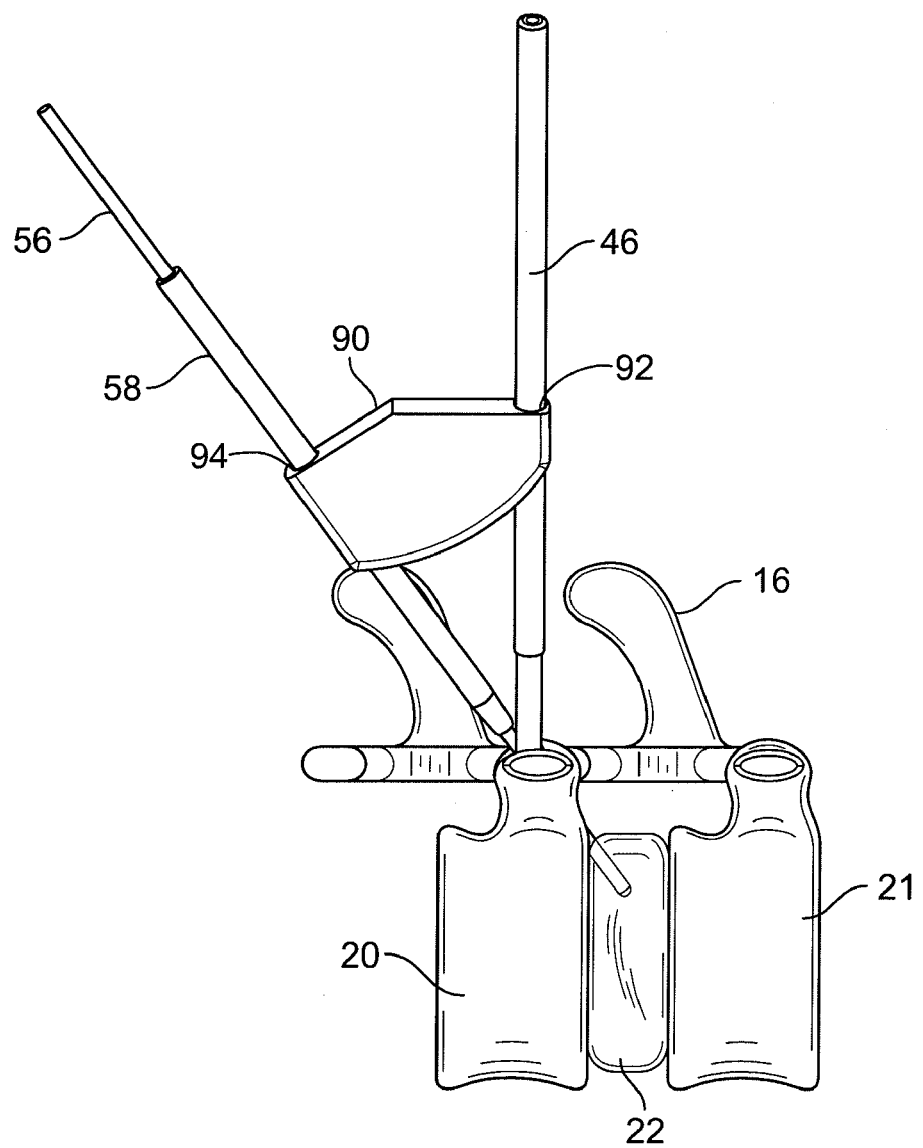
FIG. 7B is a simplified sagittal view of the vertebrae pair shown in FIG. 7A showing that the second offset angle from normal is greater than the offset angle show in FIGS. 5A to 5D according to various embodiments.

Referring to FIG. 5C the alignment tool 50 may create an offset angle of about 20 degrees of normal that may be used to form a transpedicular pathway or channel to a disc space via an inferior vertebra 20. In another embodiment it may be desirable to access the lower endplate of the superior vertebra 21 in addition to the disc space 22. FIG. 7A is a simplified isometric view of the vertebrae pair 20, 21 shown in FIG. 4D further including an offset guide pin 56 with support sleeve 58 and second transpedicular channel alignment tool 90. In this embodiment the second alignment tool 90 creates an offset angle of about 35 degrees relative to the normal port 92. In this embodiment the offset guide pin 56 and support sleeve 58 are inserted through the second transpedicular channel alignment tool's 90 offset guide port 94. The greater offset angle provided by the second alignment tool 90 may enable the guide pin to be advanced through the disc space 22 and into the lower endplate 23 of the superior vertebra 21 (see FIG. 7D) according to various embodiments. FIG. 7B is a simplified sagittal view of the vertebrae pair 20, 21 shown in FIG. 7A showing that the second offset angle from normal is greater than the offset angle show in FIGS. 5A to 5D according to various embodiments.

Figure 7C:
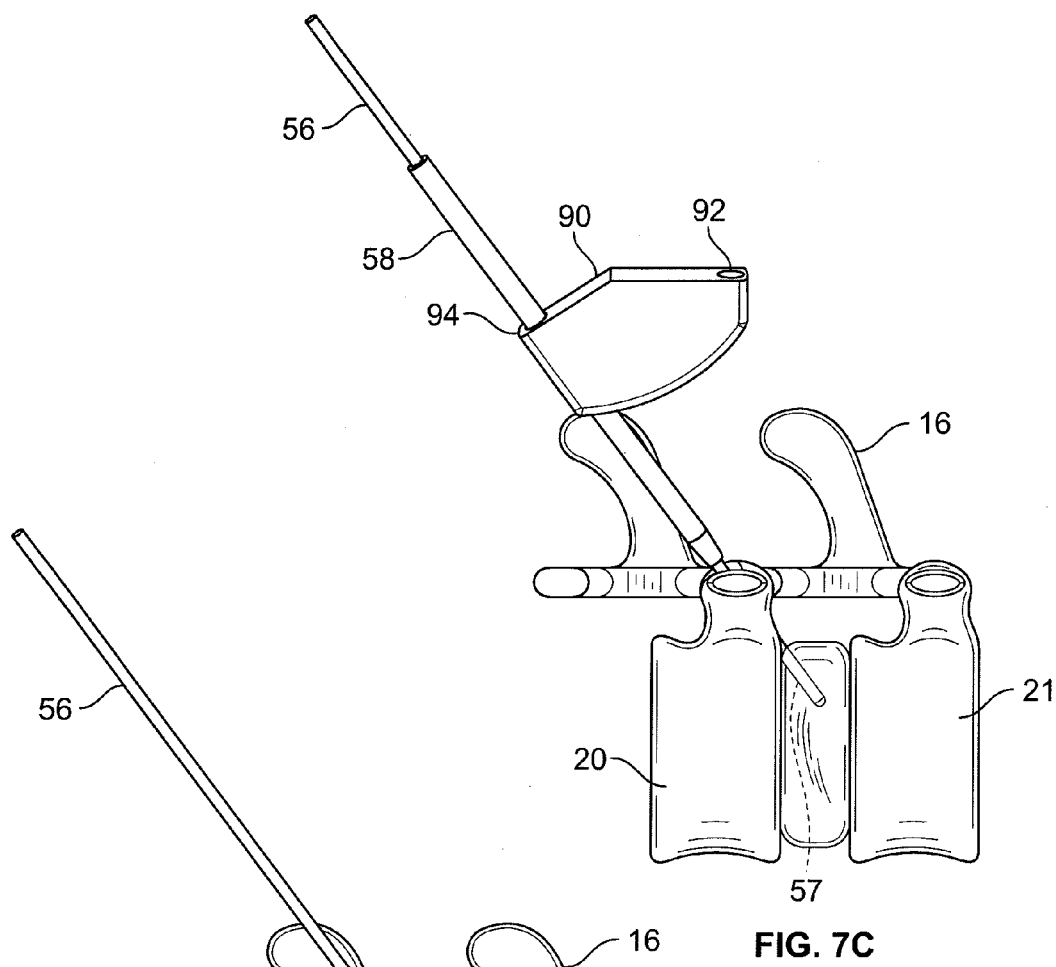
FIG. 7C is a simplified sagittal view of the vertebrae pair shown in FIG. 7B where cannula in the second transpedicular channel alignment tool's normal guide port has been removed leaving the guide pin and support sleeve inserted through the transpedicular channel alignment tool's offset guide port and the guide pin advanced at the second offset angle according to various embodiments.
Figure 7D:
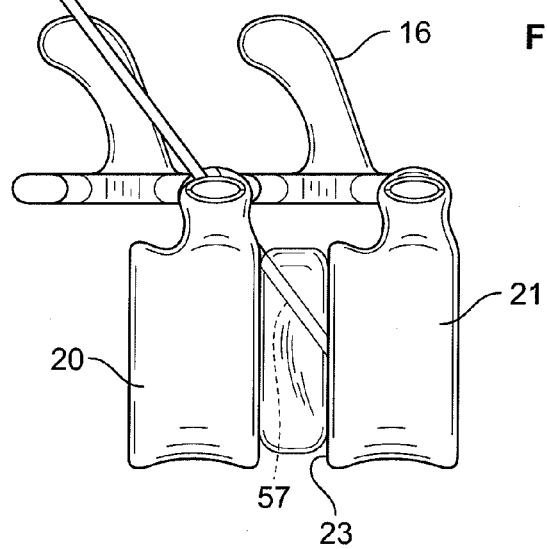
FIG. 7D is a simplified sagittal view of the vertebrae pair shown in FIG. 7C where the support sleeve in the second transpedicular channel alignment tool's offset guide port the second alignment tool have been removed leaving the guide pin inserted through a transpedicular channel to the disc space according to various embodiments.

FIG. 7C is a simplified sagittal view of the vertebrae pair 20, 21 shown in FIG. 7B where the cannula 46 in the second transpedicular channel alignment tool's 90 normal guide port 92 has been removed leaving the offset guide pin 56 and support sleeve 58 inserted through the transpedicular channel alignment tool's offset guide port 94. The offset guide pin 56 tip 57 has been inserted into the disc space 22. FIG. 7D is a simplified sagittal view of the vertebrae pair 20, 21 shown in FIG. 7C where the offset support sleeve 58 in the second transpedicular channel alignment tool's offset guide port 94 and the second alignment tool 90 have been removed leaving the guide pin 56 inserted through a transpedicular channel to the disc space 22 according to various embodiments. As described above in the formation of the transpedicular channel 66, a cannulated reamer 62 within a sleeve may be provided to create an enlarged pathway through the disc space 22 and into the endplate 23. Then a thin walled, slotted cannula 68 and obturator 67 pair may inserted over the guide pin 56 and the guide pin 56 and obturator 67 removed leaving the slotted cannula 68 extending the endplate 23.

Figure 7E:
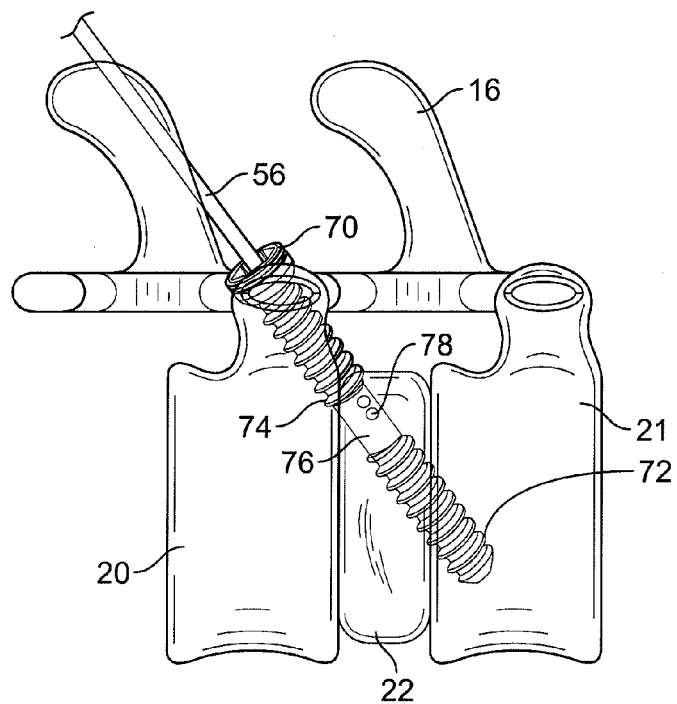
FIG. 7E is a simplified sagittal view of the vertebrae pair having a cannulated compression-distraction screw advanced over the offset guide pin or wire through the disc space into the superior vertebra via a second transpedicular channel according to various embodiments.

Via the second transpedicular channel procedures may be performed with the disc space and into the superior vertebra 21. For example, FIG. 7E is a simplified sagittal view of the vertebrae pair 20, 21 having a cannulated compression-distraction screw 70 advanced over the offset guide pin or wire 56 through the disc space into the superior vertebra via a second transpedicular channel according to various embodiments. The compression-distraction screw 70 has distal thread 72, proximal thread 74, non-threaded central section 76, and locking ports 78. In an embodiment, the distal thread 72 can be independently rotated via a head within the central section 76. In addition, in an embodiment the distal threaded portion 72 may have a sleeve within the central section 76 so the portion 72 may extend away or toward the portion 74.

Figure 7F:
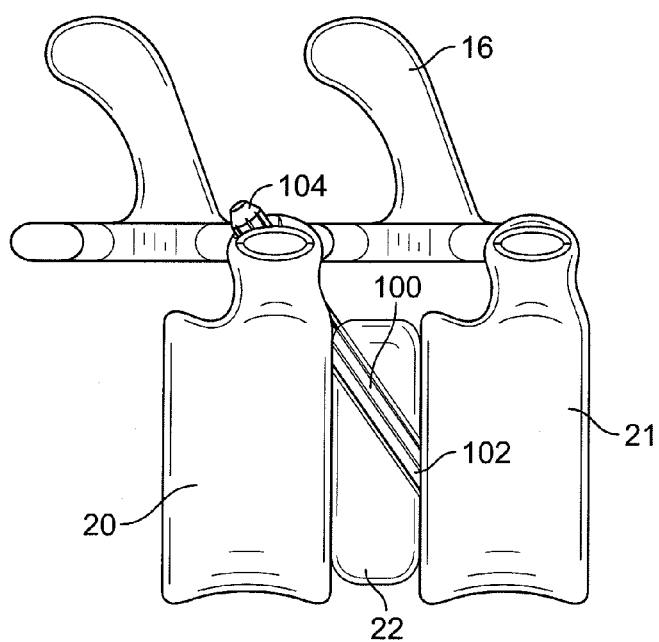
FIG. 7F is a simplified sagittal view of the vertebrae pair having a fusion construct advanced through the inferior vertebra and disc space into the superior vertebra via the second transpedicular channel according to various embodiments.

In another embodiment other instrumentation may inserted into the superior vertebra 21 via the transpedicular channel. FIG. 7F is a simplified sagittal view of the vertebrae pair 20, 21 having a fusion construct 80 advanced through the inferior vertebra 20 and disc space 22 into the superior vertebra 23 via the second transpedicular channel according to various embodiments. In this embodiment the construct 80 is a bone dowel having a proximal 84 and distal end 82. The bone dowel's 80 distal end 82 may be embedded into the superior vertebra 21 endplate 23 and its proximal end 84 in the inferior vertebra. In an embodiment a portion of the disc 22 may be removed and replaced with implants, bone growth materials, or allograft material prior to the fusion construct 80 insertion/implantation. The transpedicular channel into the superior vertebra 21 may also be used to perform kyphoplasty and other vertebra height restoration and modification procedures.

Figure 8A:
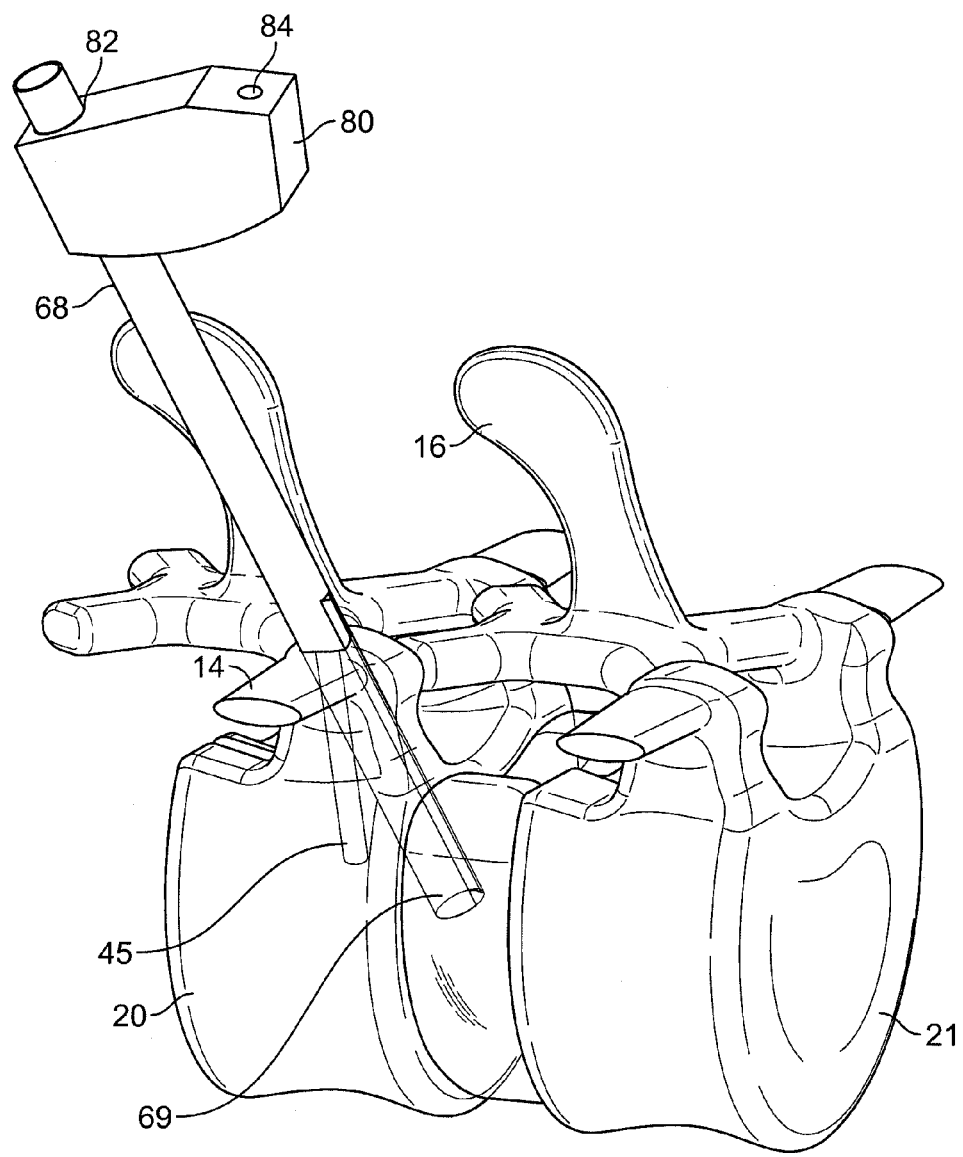
FIG. 8A is a simplified isometric view of the vertebrae pair shown in FIG. 6D including a reverse pedicle alignment tool inserted over the offset cannula according to various embodiments.
Figure 8B:
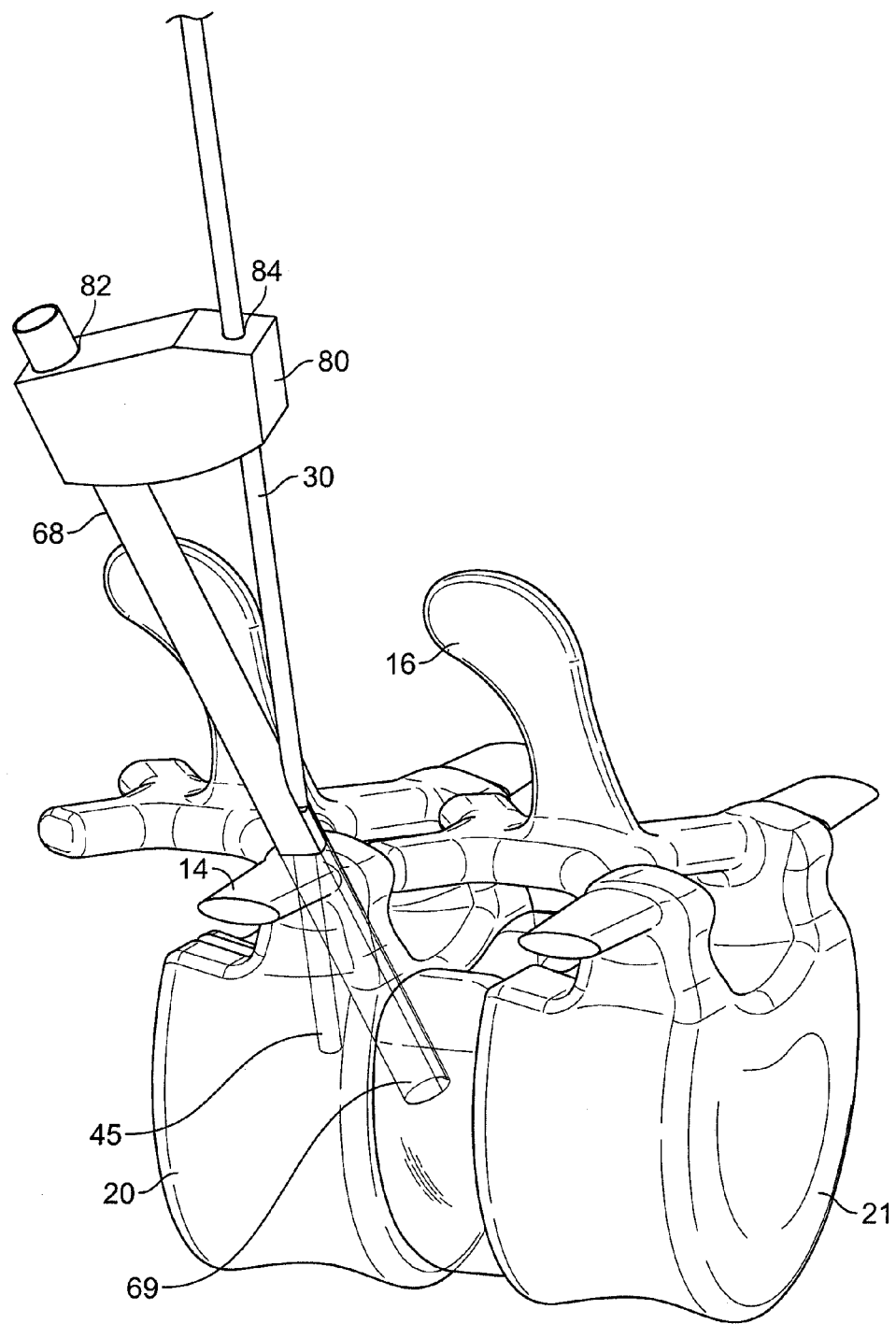
FIG. 8B is a simplified isometric view of the vertebrae pair shown in FIG. 8A including the guide pin inserted in the reverse alignment tool's normal port and through the cannula's slot according to various embodiments.

After performing one ore more procedures via the transpedicular channel, it may be desirable to access the normal pedicle channel 44 to perform one or more procedures via the normal pedicle channel 44, e.g., insertion of a pedicle screw as part fixation instrumentation. FIG. 8A is a simplified isometric view of the vertebrae pair shown in FIG. 6D including a reverse pedicle alignment tool 80 inserted over the offset cannula 68 according to various embodiments. The reverse pedicle alignment tool 80 includes an offset guide port 82 and a normal guide port 84. The offset guide port 82 is sized to fit the offset cannula 68. FIG. 8B is a simplified isometric view of the vertebrae pair shown in FIG. 8A including the guide pin 30 inserted in the reverse alignment tool's 80 normal guide port 84. In an embodiment the guide pin 30 passes through the cannula 68 slot 69.

Figure 8C:
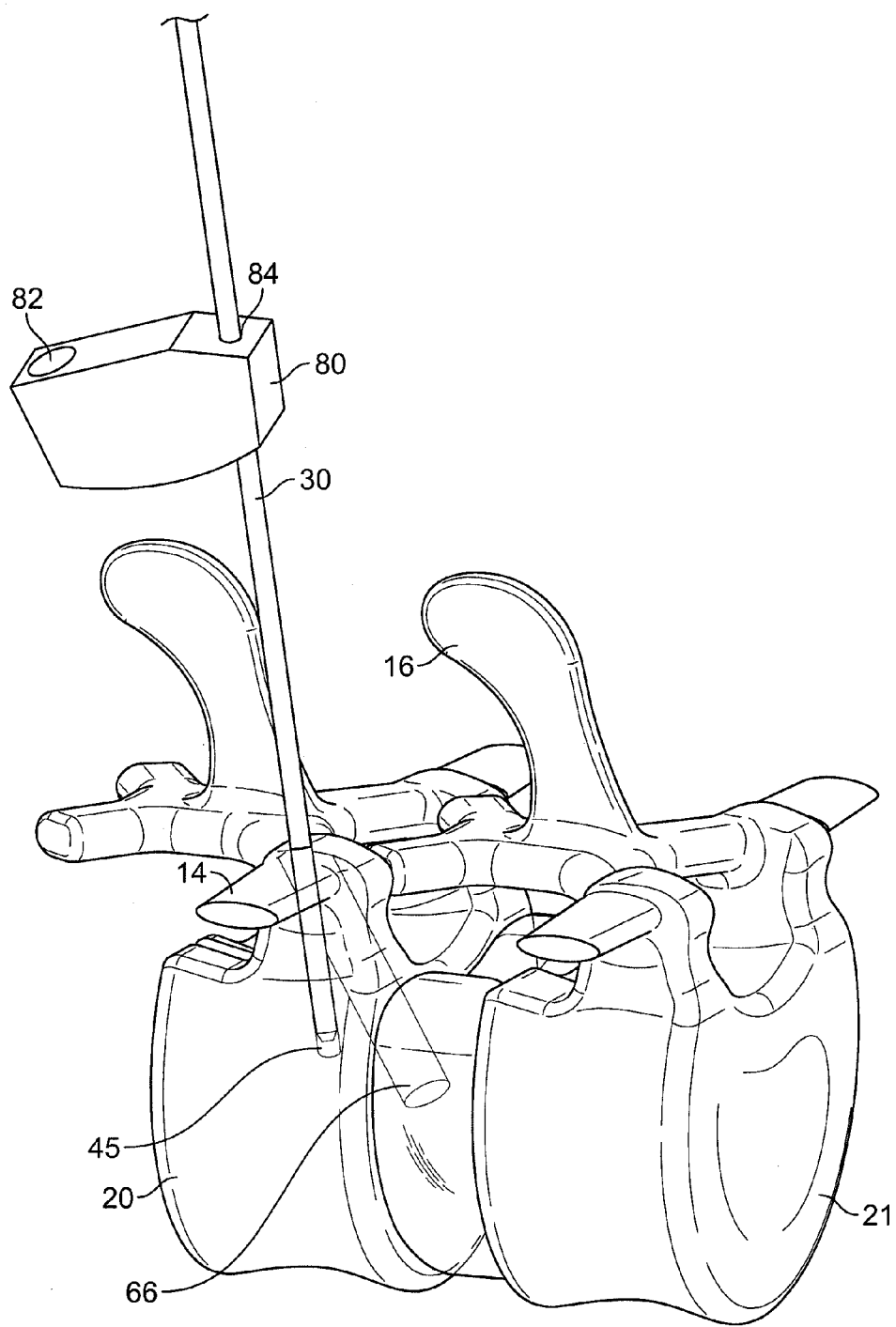
FIG. 8C is a simplified isometric view of the vertebrae pair shown in FIG. 8B where the cannula has been removed and the guide pin has been advanced into the pedicle normal channel according to various embodiments.
Figure 8D:
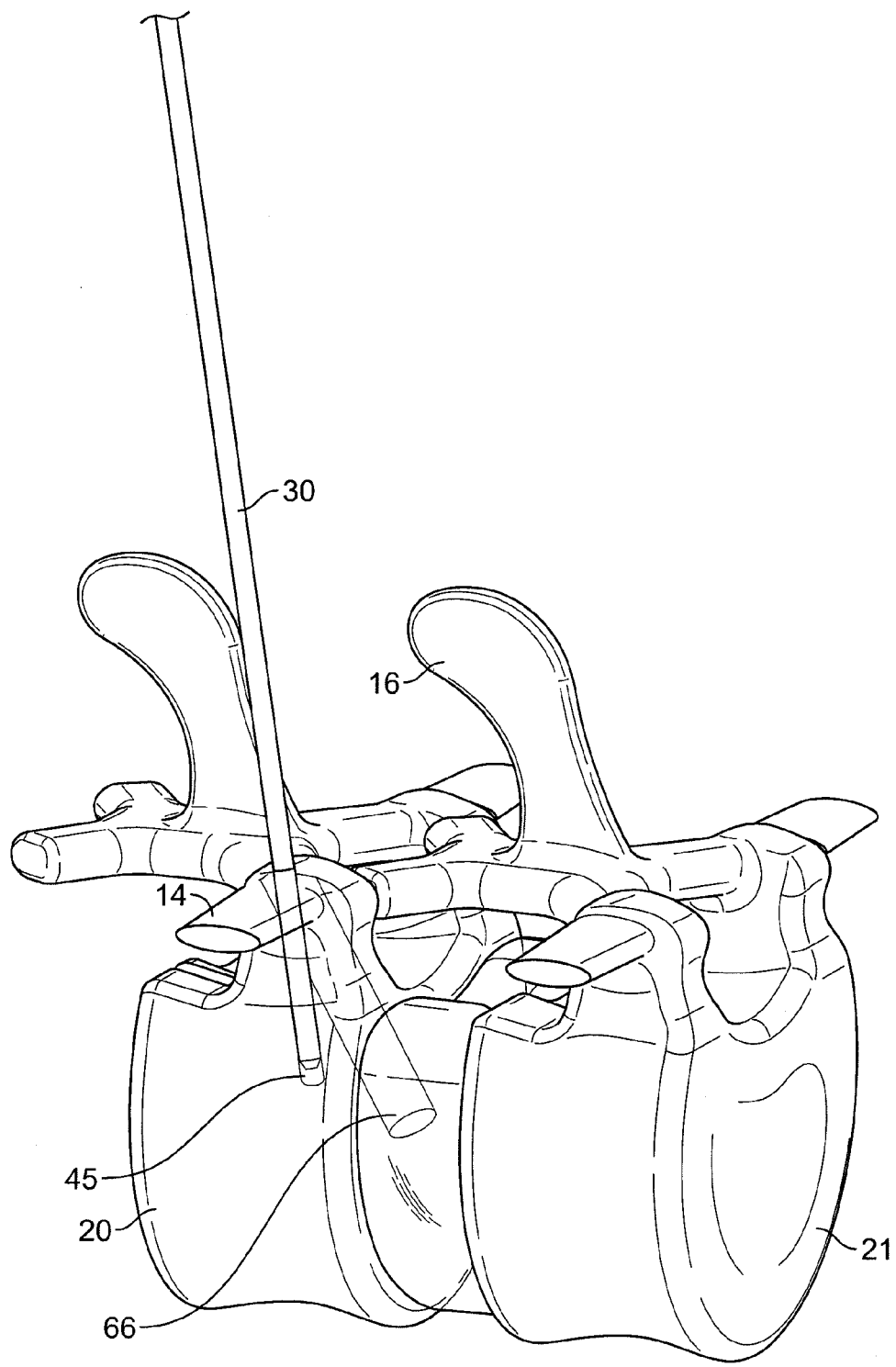
FIG. 8D is a simplified isometric view of the vertebrae pair shown in FIG. 8C where the reverse pedicle alignment tool has been removed according to various embodiments.
Figure 8E:
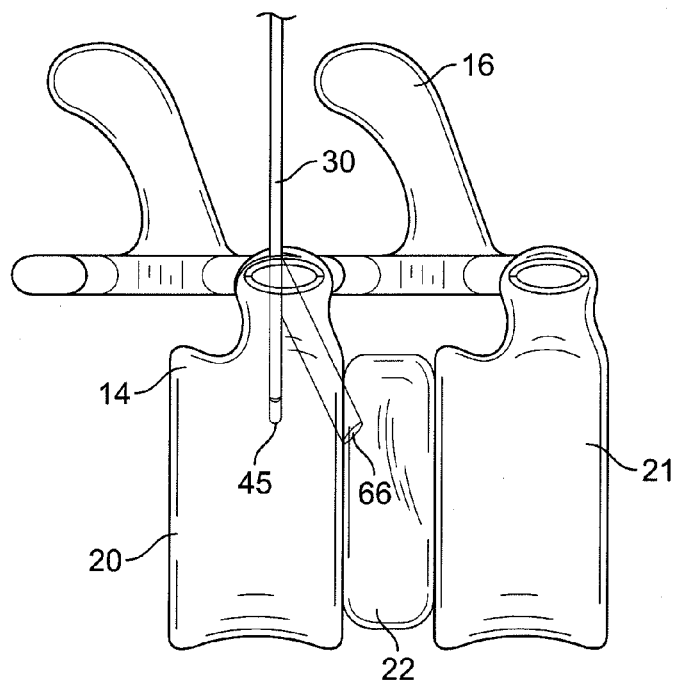
FIG. 8E is a simplified sagittal view of the vertebrae pair shown in FIG. 8D where the guide pin is inserted into the normal pedicle channel according to various embodiments.
Figure 8F:
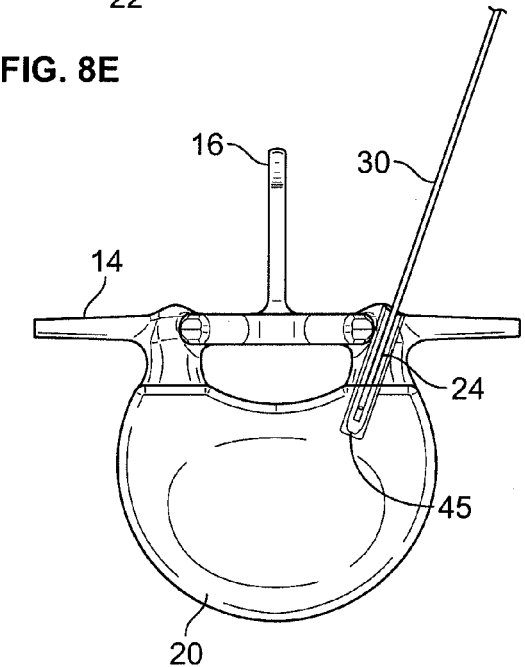
FIG. 8F is a simplified coronal view of the vertebrae pair shown in FIG. 8E where the guide pin is inserted into the normal pedicle channel according to various embodiments.

FIG. 8C is a simplified isometric view of the vertebrae pair 20, 21 shown in FIG. 8B where the offset cannula 68 has been removed and the guide pin 30 has been advanced into the pedicle normal channel 45 according to various embodiments. FIG. 8D is a simplified isometric view, FIG. 8E is a simplified sagittal view, and FIG. 8F is a simplified coronal view of the vertebrae pair 20, 21 shown in FIG. 8C where the reverse pedicle alignment tool 80 has been removed leaving the guide pin 30 in the channel 45 according to various embodiments. The guide pin 30 may then be used to access the normal pedicle channel 45 to perform one or more procedures via the normal pedicle channel 45, e.g., insertion of a pedicle screw as part fixation instrumentation.

FIGS. 9A to 9F are diagrams of another transpedicular channel alignment and access tool system 200 according to various embodiments. As shown in these FIGS., the system 200 may include a length or extension adjustable, slotted 216, cannula 210, a cannula offset tool 220, a handle 230, and an extension or length adjustment knob 240 for the cannula 210. The handle 230 may transversely (relative to cannula 10) engage the offset tool 220 via a bore 228 and handle extension 232.

Figure 9A:
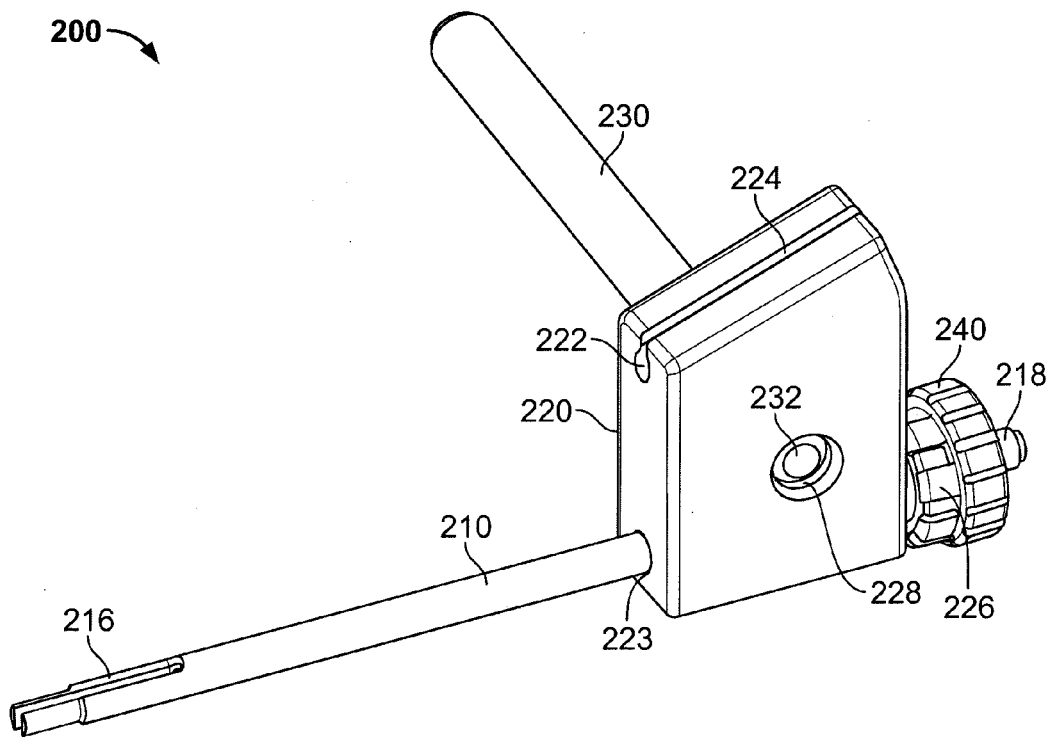
FIGS. 9A to 9F are diagrams of a transpedicular channel alignment and access tool according to various embodiments.
Figure 9B:
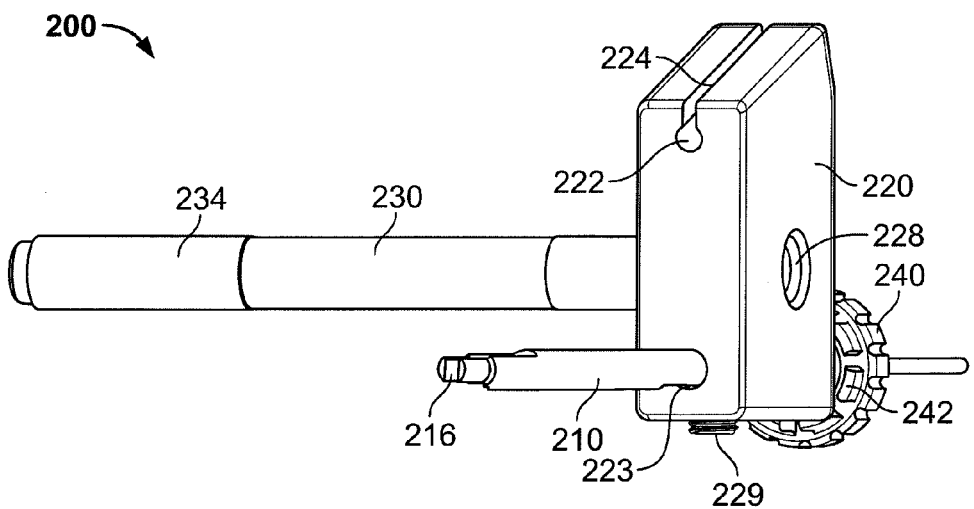
Figure 9C:
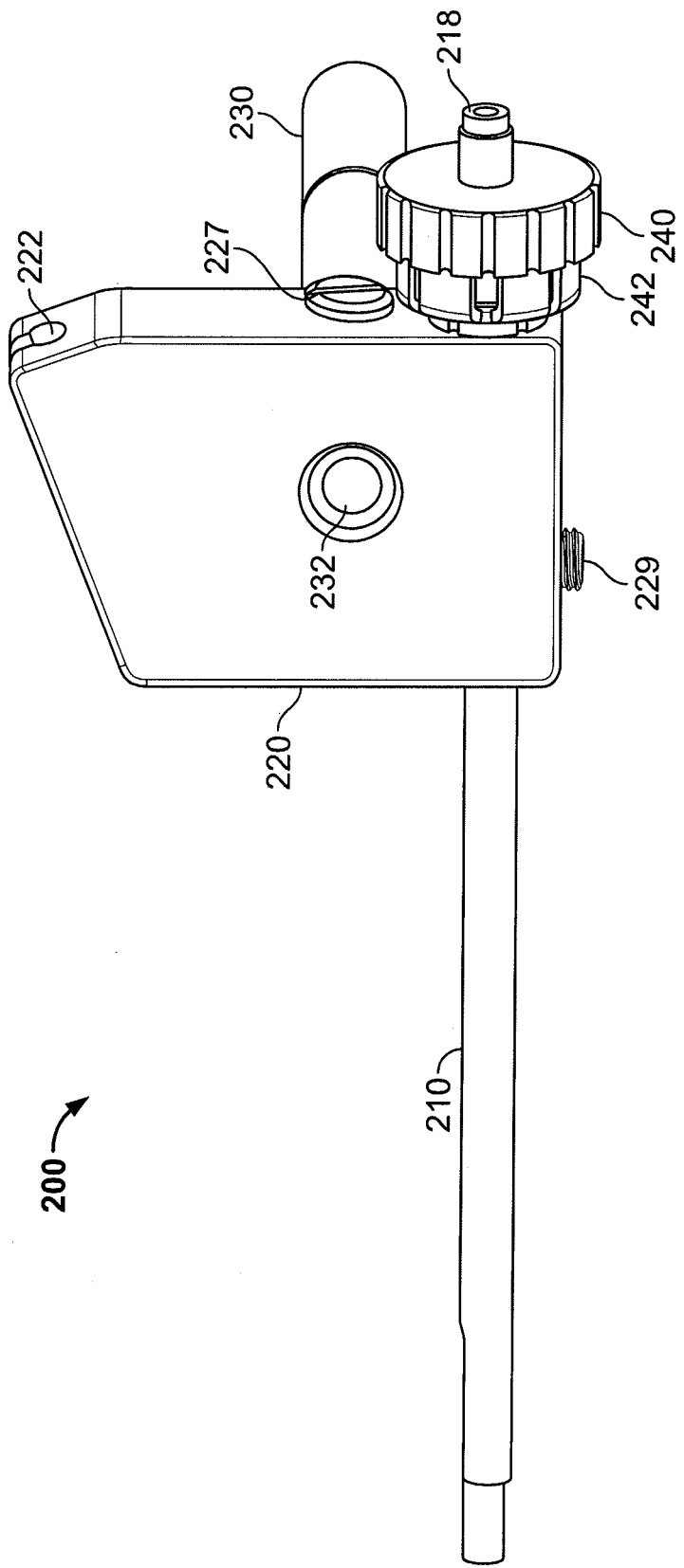
Figure 9D:
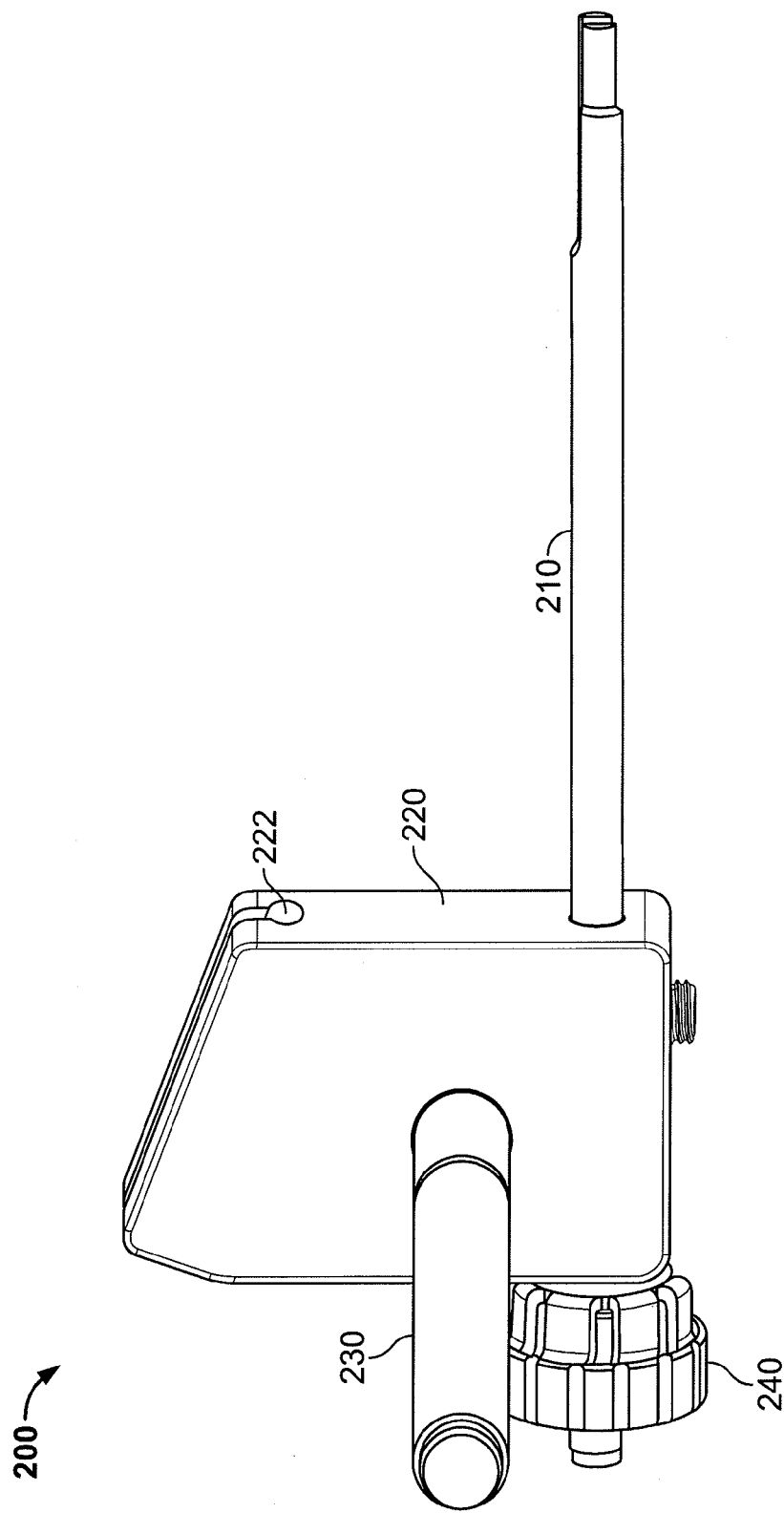
Figure 9E:
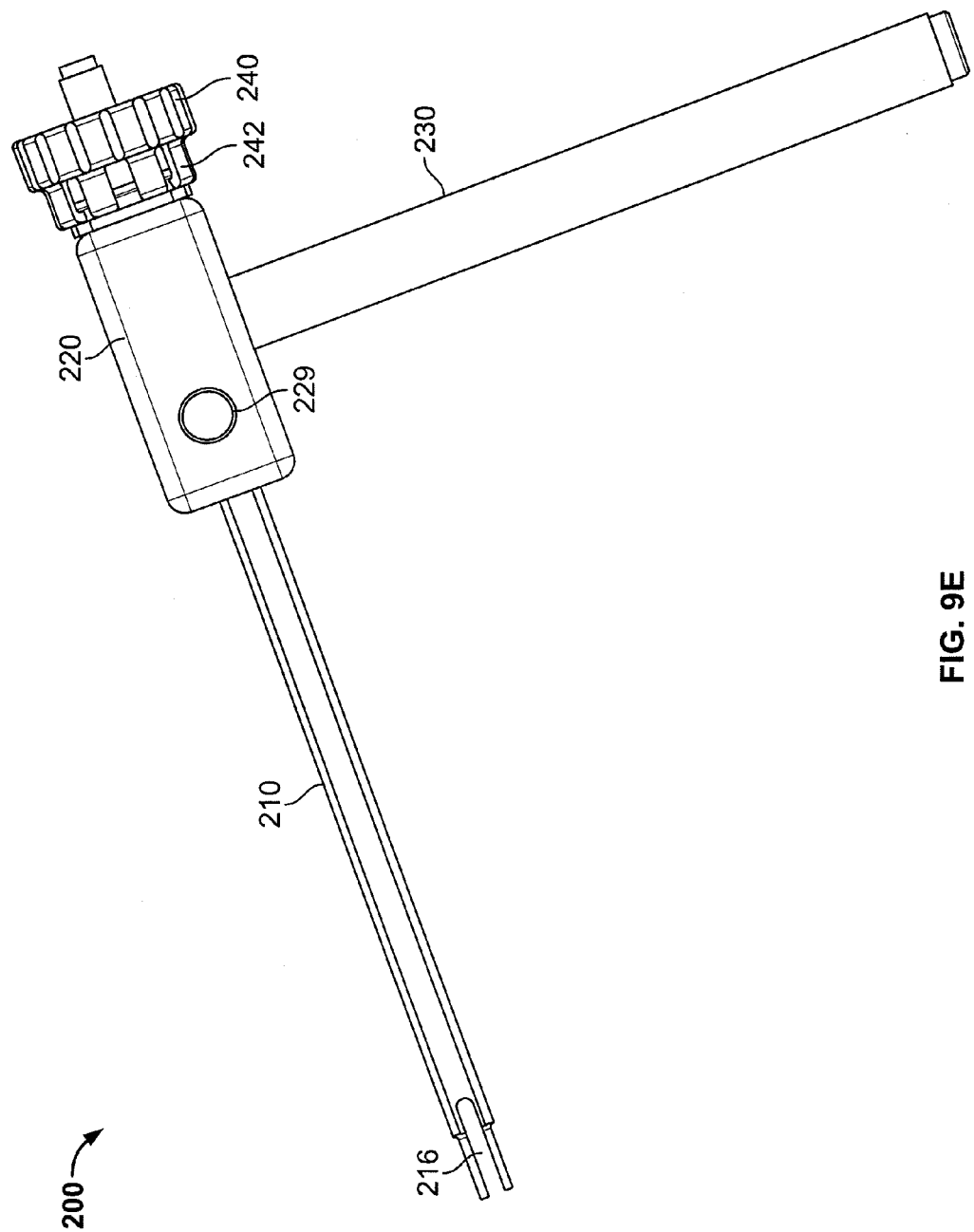
Figure 9F:
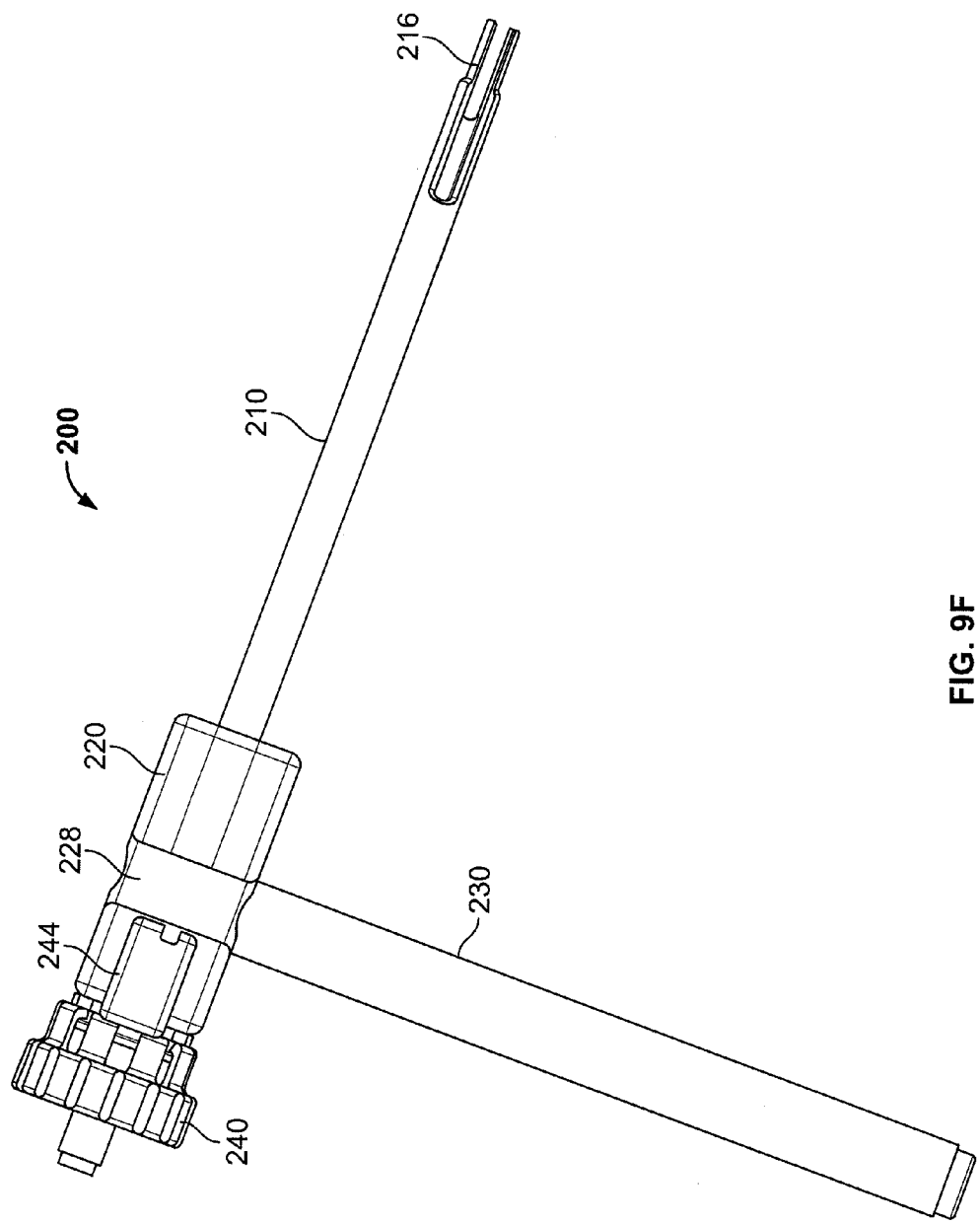
Figure 10A:
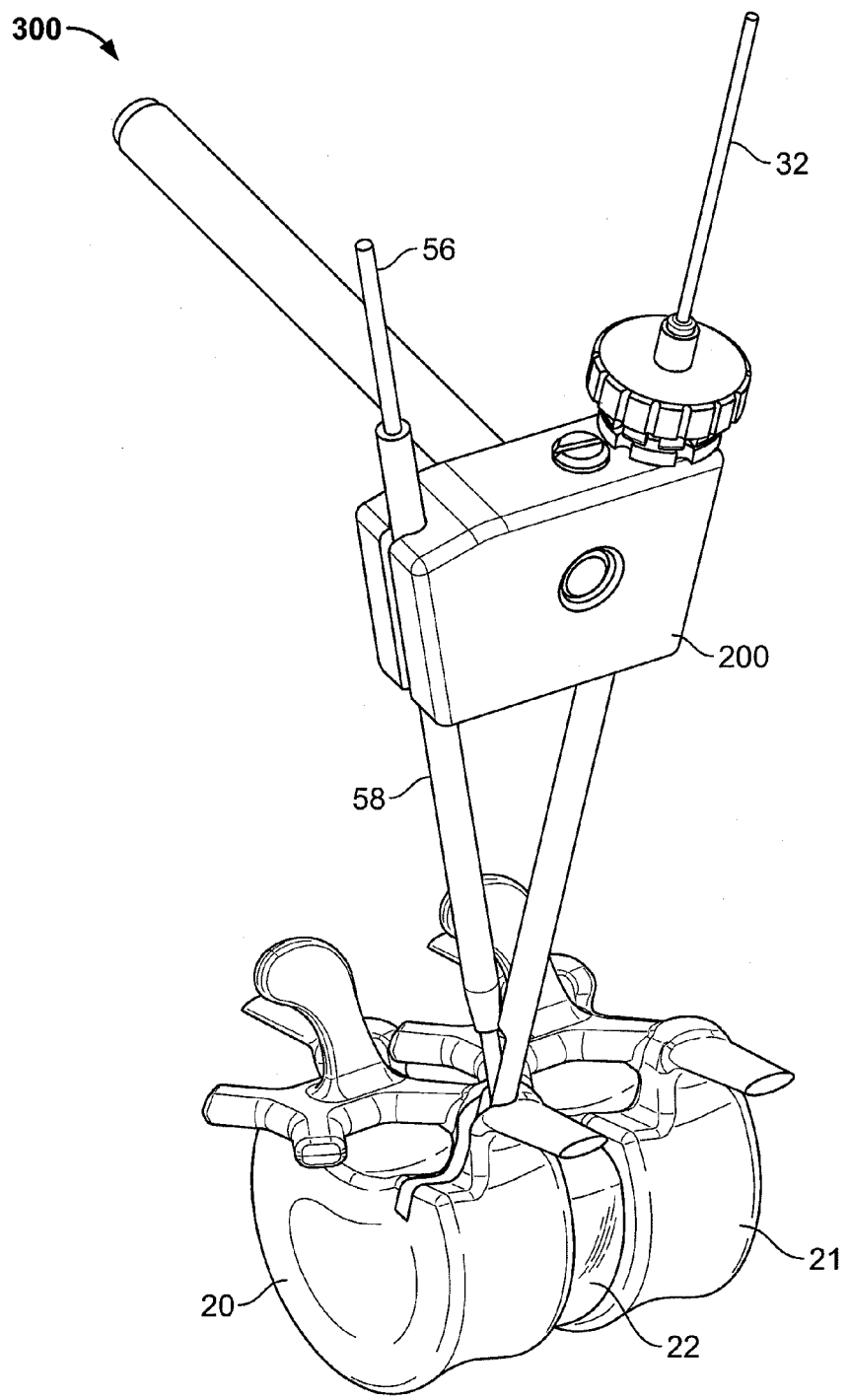
FIGS. 10A to 10F are diagrams of the transpedicular channel alignment and access tool employed in a vertebral pedicle according to various embodiments.
Figure 10B:
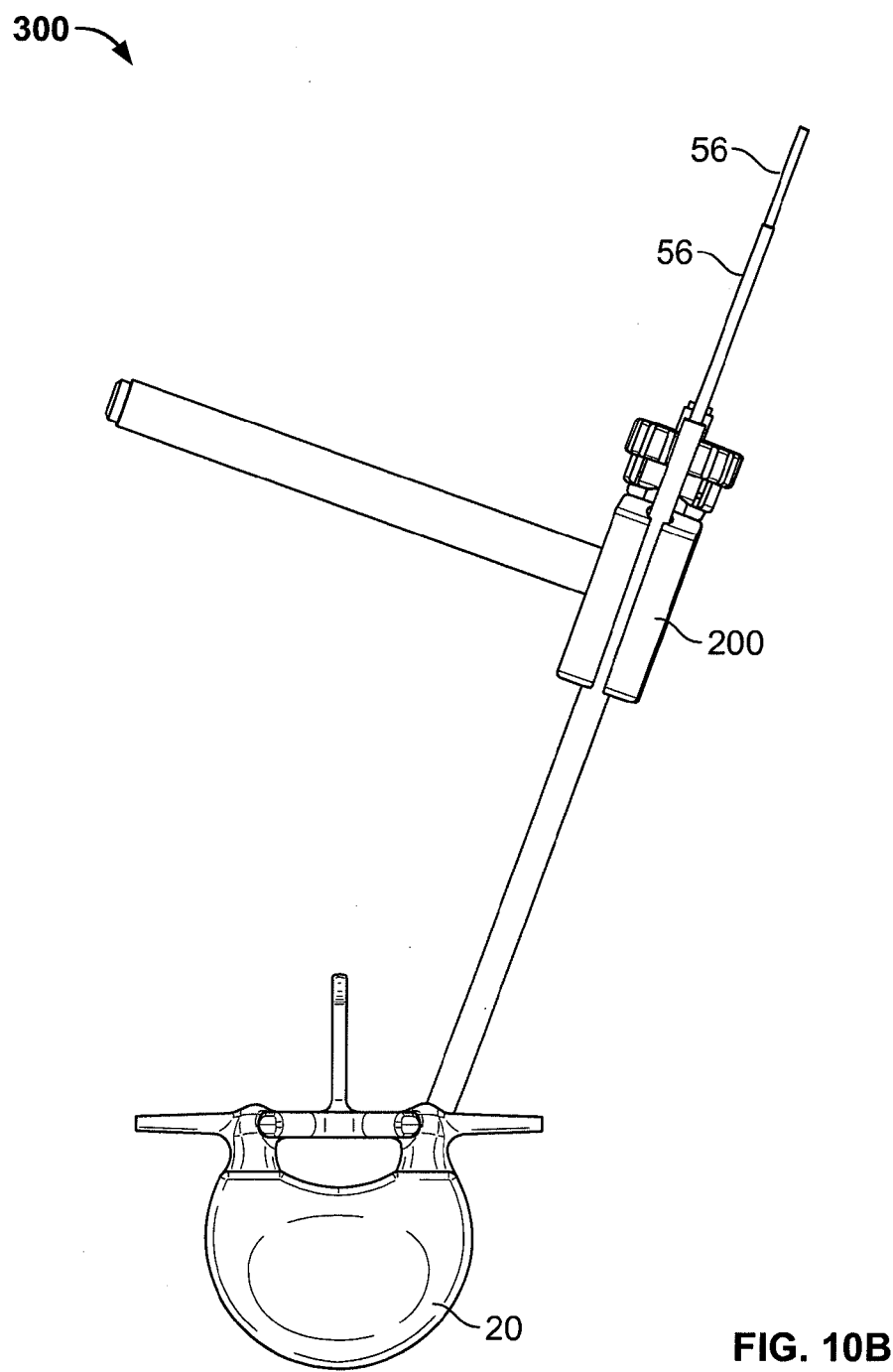
Figure 10C:
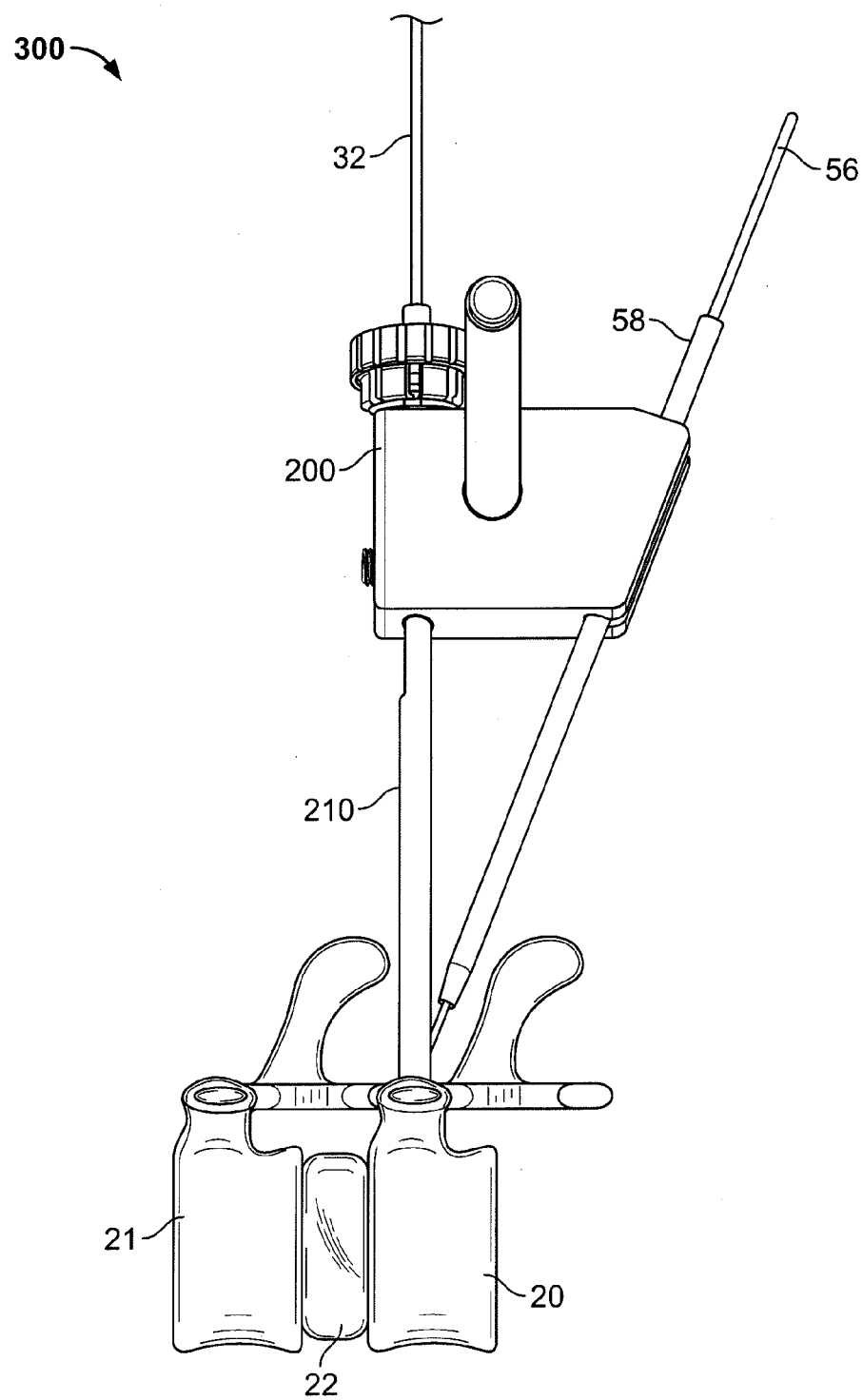
Figure 10D:
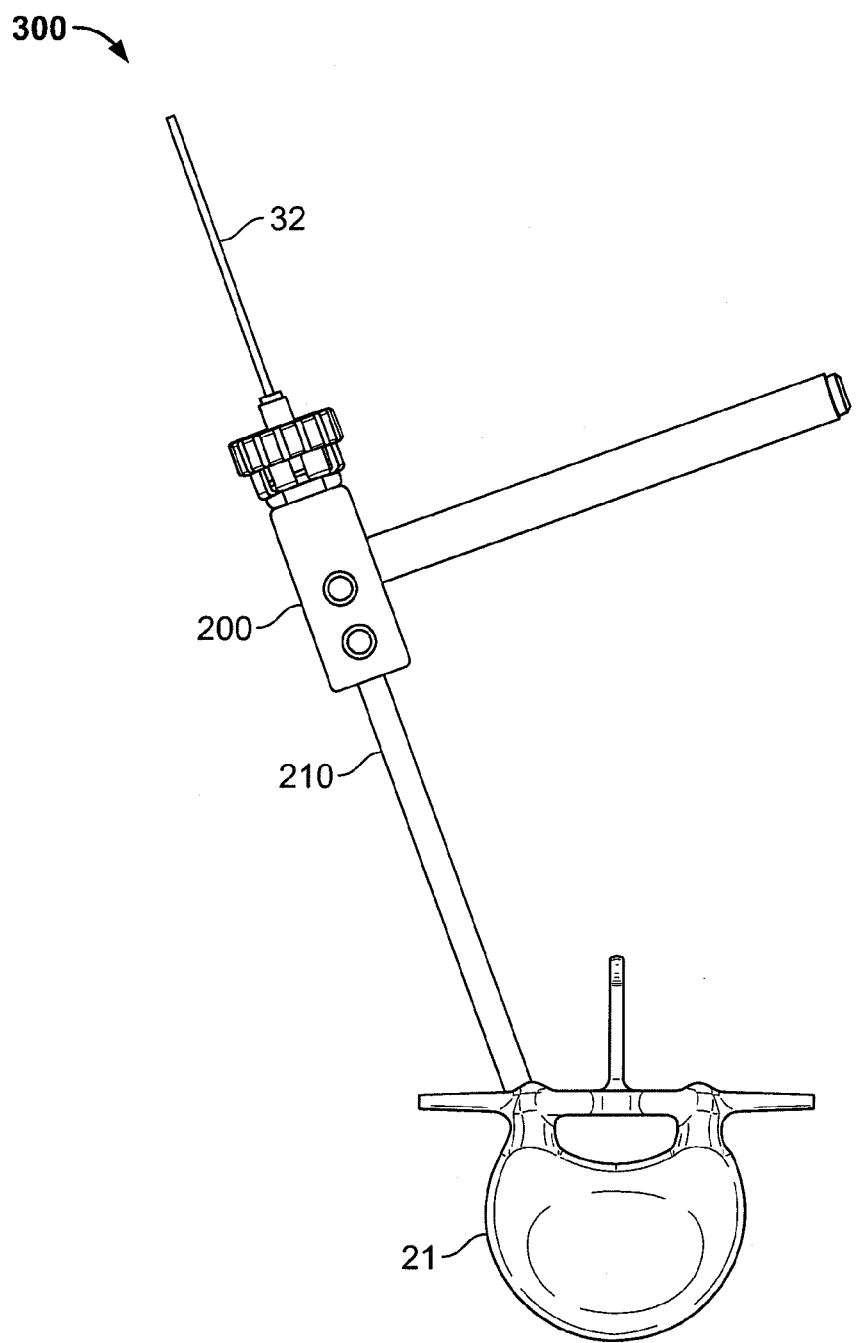
Figure 10E:
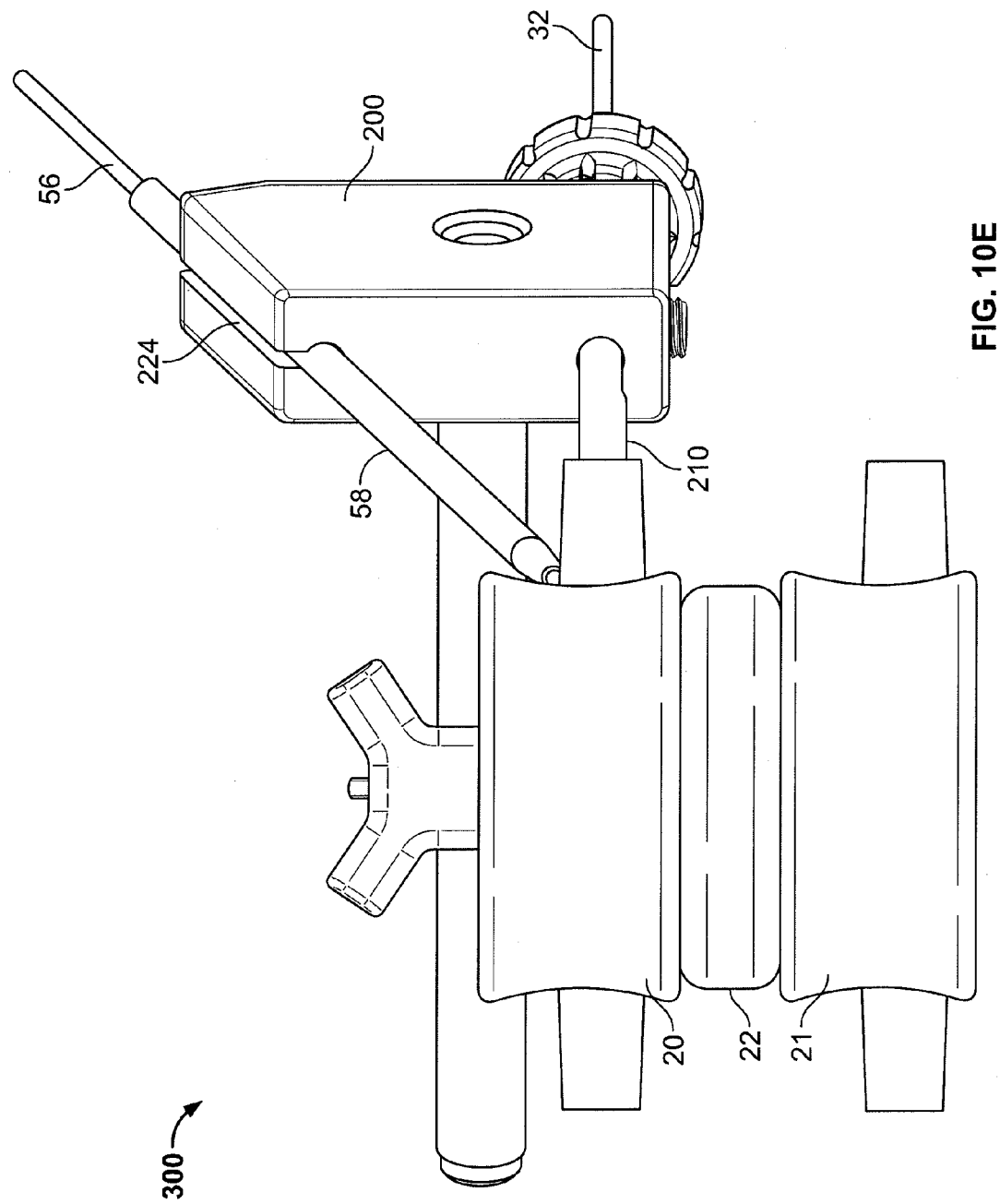
Figure 10F:
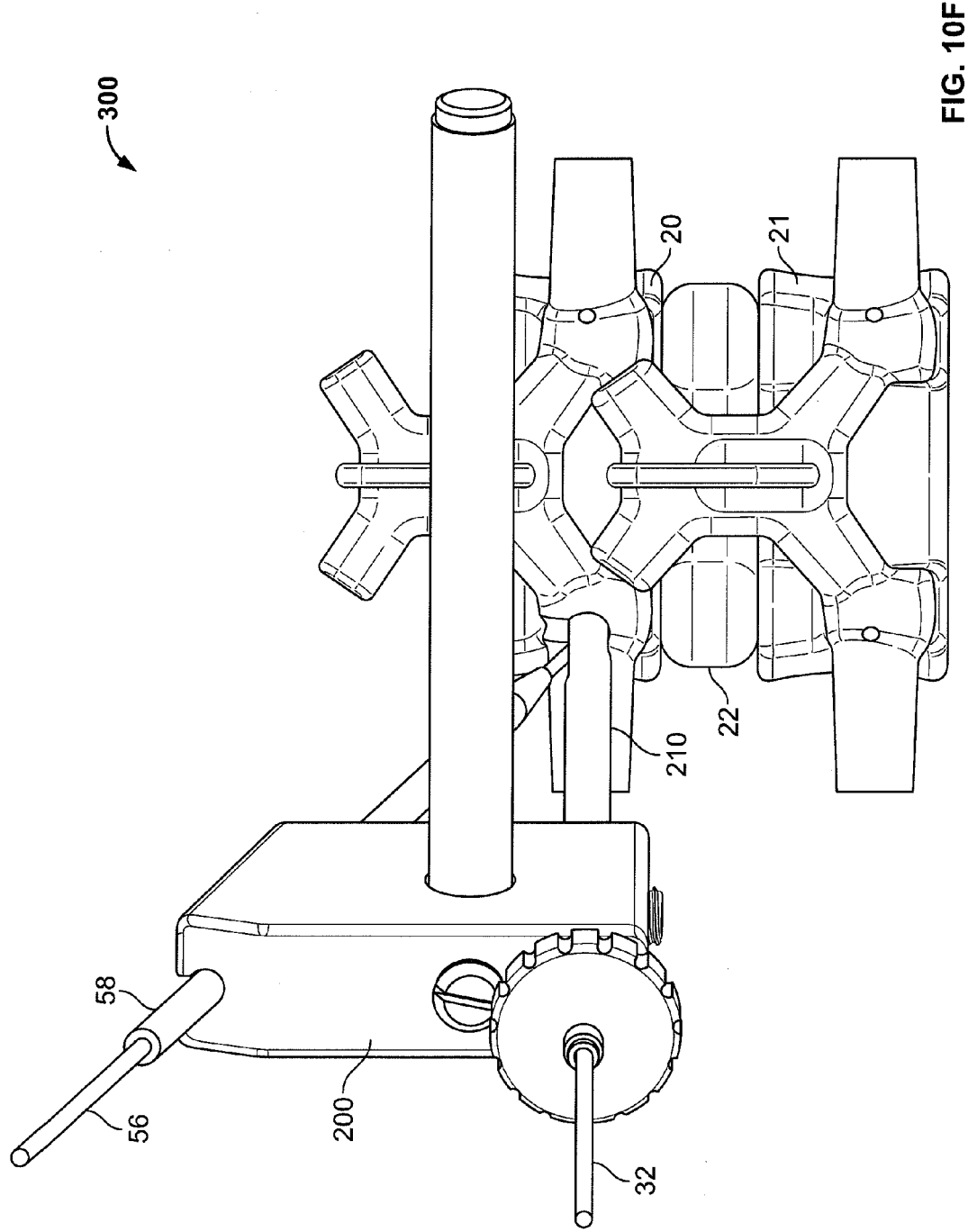

The offset tool 220 may include a first cannula channel 223 for cannula 210, a second channel 222 for a cannula or guide wire, a guide wire release slot 224, and a flange 228 for engaging one or more tabs 242 of the knob 240. As shown in FIG. 9B the handle 230 may include a larger, distal section 234. The channel 224 and cannula 210 slot 216 may be configured so a guide wire or other tool inserted into the channel 224 may pass through the cannula 210 via the slot 216. The system 200 may include a set pin or screw 229 in the offset tool 220 to fixably position the cannula 210 extension. As shown in FIG. 9C the system 200 may also include a set pin or screw 227 in the offset tool 220 to releasably engage the handle 230 so the handle extension 232 may be removed from the tool 220 channel 228. FIG. 9F includes a partial cross sectional view of the offset tool 220 showing a riser 244 that may be coupled to the knob 240 to enable translation of the cannula 210 slot 216.

FIGS. 10A to 10F are diagrams of the transpedicular channel alignment and access tool system 200 employed in a vertebra 20 according to various embodiments. The cannula 210 may be inserted normally to the spinal vertebra 20 pedicle. A guide wire 56 and cannula 58 may be placed with the slot 222 of the tool 200. The guide wire 56 and cannula 58 may be inserted into the spinal vertebra 20, disc space 22, or adjacent spinal vertebra 21 as a function of the cannula 210 slot 216 translation via the knob 40. In an embodiment the cannula 210 may have a guide wire 32 inserted therein to securely engage the cannula 210 in the spinal vertebra 20. The guide wire 32 may be partially removed to enable guide wire 56 or cannula 58 to pass through the cannula 210 slot 216 and into one of the spinal vertebra 20, disc space 22, and adjacent spinal vertebra 21.

In an embodiment the knob 240 may be rotate to linearly translate the cannula 210. The cannula 210 translation may change the offset angle between the channel 222 and cannula 210. The offset between channel 222 and cannula 210 may enable a guide wire 58 or cannula 56 to engage the vertebra 20 when knob 240 is rotated to a first point. The offset between channel 222 and cannula 210 may enable a guide wire 58 or cannula 56 to engage the disc space 22 when knob 240 is rotated to a second point. The offset between channel 222 and cannula 210 may enable a guide wire 58 or cannula 56 to engage the adjacent vertebra 21 when knob 240 is rotated to a third point.

While this invention has been described in terms of a best mode for achieving the objectives of the invention, it will be appreciated by those skilled in the art that variations may be accomplished in view of these teachings without deviating from the spirit or scope of the present invention. For example, the inferior vertebrae 20 may be the sacrum and the superior vertebrae 21 the adjacent vertebrae, L5 in humans. In addition, the apparatus and method may be performed bilaterally.

What is claimed is:

1. A method of treating the spine comprising:
   creating a first osseous channel through at least one pedicle of a first vertebra, wherein the first osseous channel is defined by a first longitudinal axis directed generally from a posterior aspect to an anterior aspect of the first vertebra, and wherein the first vertebra is located in the spine above the level of the sacrum;
   creating a second osseous channel within the pedicle, wherein the second osseous channel is defined by a second axis off-set from the first axis by an angle between about 15 degrees and 40 degrees that is directed generally from a posterior-caudal aspect to an anterior-cephalad aspect, and wherein a most posterior extent of the second osseous channel is relatively confluent with a most posterior extent of the first osseous channel;
   accessing through the second osseous channel an intervertebral disc space immediately superior to the first vertebra and immediately inferior to a second vertebra;
   placing a treatment device through the second osseous channel into or adjacent the intervertebral disc space; and
   performing a procedure within the intervertebral disc space.

2. The method of claim 1, wherein the step of performing a procedure within the intervertebral disc space comprises removing disc material through at least a portion of the second osseous channel.

3. The method of claim 1, wherein the step of performing a procedure within the intervertebral disc space comprises repairing or closing the annulus through at least a portion of the second osseous channel.

4. The method of claim 1, further comprising the step of delivering bone growth material into the disc space or immediately adjacent thereto.

5. The method of claim 1, further comprising the step of placing a fixation device through at least a portion of the first osseous channel along the first axis.

6. The method of claim 5, wherein the fixation device comprises a pedicle screw.

7. The method of claim 5, wherein the fixation device extends from the first vertebra to threadably engage the second vertebra.

8. The method of claim 5, wherein the fixation device threadably engages the first vertebra and does not threadably engage the second vertebra.

9. The method of claim 1, further comprising the step of placing a fixation device through at least a portion of the second osseous channel along the second axis.

10. The method of claim 1, wherein placing the treatment device comprises placing the device through the second osseous channel into an adjacent foramen.

11. The method of claim 1, wherein placing the treatment device comprises placing the device through the second osseous channel into an adjacent annulus.

12. The method of claim 1, further comprising the step of placing a device through at least a portion of the first osseous channel along the first axis or the second osseous channel along the second axis, wherein the device is selected from the group consisting of a fixation, load-bearing, articulating, and therapeutic agent dispensing device.

13. The method of claim 12, wherein the articulating device links the first vertebra to the second vertebra.

14. The method of claim 12, wherein the load-bearing device is at least partially positioned between the first vertebra and the second vertebra.

15. The method of claim 12, wherein the therapeutic agent dispensing device extends from the pedicle of the first vertebra adjacent to or into the adjacent disc space.

16. The method of claim 1, wherein the most posterior extent of the first osseous channel and the most posterior extent of the second osseous channel form a common access hole on the first vertebra.

17. The method of claim 16, wherein the common access hole is located on the pedicle of the first vertebra.

18. The method of claim 17, wherein the common access hole is located near the root of a transverse process of the first vertebra.

19. A method of treating the spine comprising:
   employing a surgical guide comprising a stabilizing guide element, an off-axis guide element, and an arcuate linkage element that couples the stabilizing guide element to the off-axis guide element;
   placing the stabilizing guide element generally along a first longitudinal axis directed from a posterior aspect to an anterior aspect of a pedicle of a first vertebra; and
   positioning the off-axis guide element generally along a second longitudinal axis, wherein the second longitudinal axis is off-set from the first longitudinal axis by an angle between about 15 degrees and 40 degrees and wherein a most posterior extent of the second axis is generally confluent with a most posterior extent of the first axis creating a first intraosseous channel through the pedicle of the first vertebra using a stabilizing guide element, the first channel directed along the first longitudinal axis; and
   creating a second intraosseous channel within the pedicle, wherein the second intraosseous channel has a second longitudinal axis directed generally from a posterior-caudal aspect to an anterior-cephalad aspect, and wherein a most posterior extent of the second intraosseous channel is relatively confluent with a most posterior extent of the first intraosseous channel.

20. The method of claim 19, wherein creating the first intraosseous channel through the pedicle of the first vertebra comprises using a guide pin, drill or alternative osseous channel defining element positioned through the stabilizing guide element and generally along the first axis.

21. The method of claim 20, wherein creating the second intraosseous channel through the pedicle of the first vertebra comprises using a guide pin, drill or alternative osseous channel defining element positioned through the off-set guide element and generally along the second axis.

22. The method of claim 21, further comprising accessing through the second intraosseous channel an intervertebral disc space immediately superior to the first vertebra and immediately inferior to a second vertebra.

23. The method of claim 22, further comprising placing a treatment device through the second intraosseous channel into or adjacent the intervertebral disc space.

24. The method of claim 23, further comprising performing a procedure within the intervertebral disc space.

25. The method of claim 24, further comprising placing a fixation device through at least a portion of the first intraosseous channel.

26. The method of claim 24, wherein the step of performing a procedure within the intervertebral disc space comprises removing disc material through at least a portion of the second intraosseous channel.

27. The method of claim 24, wherein the step of performing a procedure within the intervertebral disc space comprises repairing or closing the annulus through at least a portion of the second intraosseous channel.

28. The method of claim 24, further comprising the step of delivering bone growth material into the disc space or immediately adjacent thereto.

29. The method of claim 24, further comprising the step of delivering therapeutic material for cartilage repair into the disc space or immediately adjacent thereto.

30. The method of claim 19, wherein the stabilizing guide element further comprises a cannula having a bifurcation at a distal end region.

31. The method of claim 30, wherein placing the stabilizing guide element generally along the first longitudinal axis comprises placing the stabilizing guide element over a guide pin positioned within the pedicle of the first vertebra, wherein the guide pin is positioned generally along the first axis.

32. The method of claim 31, wherein a portion of the cannula is placed within the first intraosseous channel.

33. The method of claim 30, wherein a guide pin extending through the off-axis guide element along the second axis is inserted through the bifurcation.

34. The method of claim 33, further comprising linearly translating the cannula along the first axis and relative to the guide pin inserted through the bifurcation, wherein the cannula is translated by an actuator coupled thereto.

35. The method of claim 34, wherein linear translation of the cannula comprises adjusting the angle between the first axis and the second axis.

36. The method of claim 33, wherein the arcuate linkage element couples the stabilizing guide element and the off-axis guide element such that the guide pin adjustably intersects the bifurcation at the distal end region of the cannula.

37. The method of claim 19, wherein the first vertebra is above the level of the sacrum.

* * * * *